(12) United States Patent
Ewin et al.

(10) Patent No.: US 12,209,084 B2
(45) Date of Patent: Jan. 28, 2025

(54) SEROTONIN 5-HT2B INHIBITORY COMPOUNDS

(71) Applicant: Zoetis Services LLC, Parsippany, NJ (US)

(72) Inventors: Richard A. Ewin, Kalamazoo, MI (US); Ashley E. Fenwick, Naperville, IL (US); Govindan Subramanian, Belle Mead, NJ (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 17/870,885

(22) Filed: Jul. 22, 2022

(65) Prior Publication Data

US 2023/0071039 A1 Mar. 9, 2023

Related U.S. Application Data

(60) Provisional application No. 63/225,775, filed on Jul. 26, 2021.

(51) Int. Cl.
| | | |
|---|---|---|
| *C07D 451/04* | (2006.01) | |
| *A61P 9/04* | (2006.01) | |
| *C07D 519/00* | (2006.01) | |

(52) U.S. Cl.
CPC .............. *C07D 451/04* (2013.01); *A61P 9/04* (2018.01); *C07D 519/00* (2013.01)

(58) Field of Classification Search
CPC .............................. C07D 451/04; C07D 519/00
See application file for complete search history.

(56) References Cited

U.S. PATENT DOCUMENTS

| | | |
|---|---|---|
| 8,012,956 B2 | 9/2011 | Rice et al. |
| 8,609,696 B2 | 12/2013 | Cogan et al. |
| 2004/0138286 A1* | 7/2004 | Imazaki ............ A61P 9/12 548/503 |
| 2017/0058349 A1 | 3/2017 | Levy et al. |
| 2022/0162183 A1 | 5/2022 | Ewin et al. |

FOREIGN PATENT DOCUMENTS

WO WO-2008016811 A2 * 2/2008 ........... C07D 401/12

OTHER PUBLICATIONS

Pascal Bonaventure, et al., "Molecular and pharmacological characterization of serotonin 5-HT2A and 5-HT$_{2B}$ receptor subtypes in dog," European Journal of Pharmacology 513 (2005), pp. 181-192.
Fabrice Jaffré, MS, et al., "Involvement of the Serotonin 5-HT$_{2B}$ Receptor in Cardiac Hypertrophy Linked to Sympathetic Stimulation Control of Interleukin-6, Interleukin-1β, and Tumor Necrosis Factor-α Cytokine Production by Ventricular Fibroblasts," Circulation, American Heart Association, vol. 110, No. 8, Aug. 24, 2004, pp. 969-974.

* cited by examiner

Primary Examiner — Susanna Moore
(74) Attorney, Agent, or Firm — Paul M. Misiak

(57) ABSTRACT

The invention describes novel serotonin c5-HT2B receptor antagonists of Formula (1), and pharmaceutically acceptable salts thereof; wherein Ring A, L, X, X',

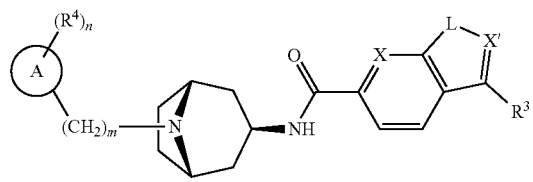

(1)

$R^3$, $R^4$, m and n are as defined herein. Also described are compositions comprising a Formula (1) compound, or a pharmaceutically acceptable salt thereof; and methods of using the compounds, or a pharmaceutically acceptable salt thereof, for the treatment of myxomatous mitral valve disease (MMVD), congestive heart failure (CHF) and/or asymptomatic heart failure in animals, preferably is a canine.

21 Claims, No Drawings

SEROTONIN 5-HT2B INHIBITORY COMPOUNDS

FIELD OF THE INVENTION

This invention describes novel compounds that are serotonin 5-HT2B receptor antagonists useful for the treatment of mitral valve disease and congestive heart failure in animals. The invention also describes compositions comprising a compound of the invention, and pharmaceutically acceptable salts thereof, as well as methods of using said compound for treating animals with mitral valve disease, congestive heart failure and/or asymptomatic heart failure.

BACKGROUND

The serotonin 5-HT2B receptor was first characterized as the serotonogenic G protein-coupled receptors that controlled contraction in the rat stomach fundus (Clineschmidt, et al., 1985, J. Pharmacol. Exp. Ther., 235, 696). 5-HT2B has since been detected in human tissues including adipose tissue, central nervous system, heart, liver, intestine, lung, skeletal muscle, spleen and other organs and tissues (Kursar et al., 1994, Mal. Pharmacol., 46, 227; Sanden et al., 2000, Neurochem Int., 36, 427-435; Borman et al., 2002 Br. J. Pharmacol., 135, 1144; Schmuck et al., 1994, FEES Lett., 342, 85) and in dog tissues including the lungs, heart, smooth muscle, and brain (Bonaventure et. al, Eur J. Pharmacol. 2005 Apr. 25, 513(3) 181-192; Oyama et. al., J. Vet. Intern. Med. 2010, 24, 27-36). Modulators of 5-HT2B that include antagonists, partial antagonists, inverse agonists, and 5-HT2B desensitizers, can be used as treatments for disorders in these tissues in which activation of 5-HT2B has a direct or indirect role.

Control of serotonin (5-hydroxytryptamine, 5HT) levels and signaling is used to treat disorders of the central nervous system, intestinal contraction and motility, and vascular function. 5-HT has a role in vascular contraction and relaxation, and can impact vascular function, growth, and morphology. Wild-type mice develop symptoms of pulmonary arterial hypertension (PAH) under hypoxic conditions while 5-HT2B receptor knock-out mice do not, suggesting that modulation of 5-HT2B may alleviate PAH. The phenotype of 5-HT2B receptor knock-out mice demonstrates the importance of this receptor for heart development. Surviving mice possess under-developed hearts resulting from impaired myocyte proliferation (Nebigil, et. al., 2001, Circulation, 103, 2973). Conversely, 5-HT2B over expression in mice leads to cardiac hypertrophy (Nebigil, et. al., 2003, Circulation, 107 (25), 3223). Selective 5-HT2B antagonists prevent isoproterenol induced cardiac hypertrophy (Jaffre et al., 2004, Circulation, 110, 969). More recently, genomics data from a model of tachypacing-induced decompensatory heart failure in dogs showed an up-regulation of 5-HT2B mRNA (Ojaimi et. al., 2007, Physiol. Genomics 29, 76). Therefore, modulation of 5-HT2B may treat disorders associated with cardiac hypertrophy such as congestive heart failure. In fact, in both humans and experimental animal models, increased serotonin signaling can induce valvular interstitial cell differentiation and myxomatous valve damage.

Myxomatous mitral valve disease (MMVD) is the leading cause of cardiovascular disease in dogs. MMVD causes incompetence of the mitral valve leading to mitral regurgitation which promotes sodium and water retention, activation of neurohormonal systems, volume overload, and eventual congestive heart failure (CHF). Synonymous MMVD medical terms used herein, include mitral valve disease (MVD), degenerative mitral valve disease (DMVD); chronic valve disease (CVD); chronic valvular heart disease (CVHD); and atrial ventricular valvular insufficiency (AVVI). The pathology of MMVD involves the differentiation and activation of the normally quiescent mitral interstitial cells into a more active myofibroblast phenotype, which mediates many of the histological and molecular changes in the valve tissue. MMVD is present in approximately 30% of all dogs over the age of 10 years and is the most frequent cause of CHF in dogs. MMVD is most prevalent in small dogs, and breeds such as the Cavalier King Charles Spaniel, Chihuahua, Maltese, Pekinese, toy and miniature poodles. The natural history of the disease is one of adult onset, variable progression with aging, and eventual development of CHF in dogs with severe disease.

Current treatment for MMVD includes angiotensin enzyme inhibitors, diuretics, vasodilators, and positive inotropes which center on symptomatic relief rather than arresting disease progression. Further, some of these treatments pose additional adverse risks to the animal, for example: loss of appetite, lethargy, altered heart function (e.g., polarization) and renal damage. The Formula (1) compounds of the instant invention have an affinity for canine 5-HT2B (c5-HT2B) receptors and may provide for a newer and safer drug therapy to veterinarians for treating canine patients with MMVD to slow or halt the progression of MMVD, CHF and/or asymptomatic heart failure.

SUMMARY OF THE INVENTION

In one aspect of the invention, are novel serotonin canine 5HT2B (c5-HT2B) receptor antagonists useful for the treatment of myxomatous mitral valve disease, congestive heart failure and/or asymptomatic heart failure in animals, particularly canines. In another aspect, is a composition comprising a compound of the invention, or a pharmaceutically acceptable salt thereof, and optionally a pharmaceutically acceptable excipient, for treating animals, preferably canine, with MMVD, CHF and/or asymptomatic heart failure.

In one aspect of the invention, is a Formula (1) compound,

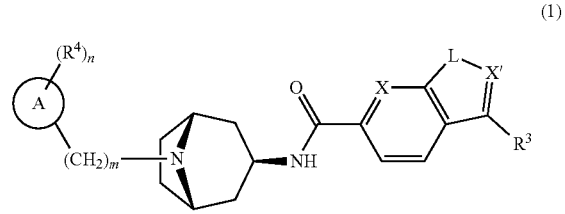

(1)

wherein X is CH or N;
L is $NR^1$ or O;
X' is $CR^2$ or N;
$R^1$ is H, $C_1$-$C_6$alkyl, phenyl or pyridinyl, and wherein the phenyl or pyridinyl are each optionally substituted with one or two $R^4$ substituents;
$R^2$ is H, $C_1$-$C_4$alkyl, —$CF_3$ or halo;
$R^3$ is H, cyano, halo, $C_1$-$C_4$alkyl or —$CF_3$;
or $R^2$ and $R^3$ join together to form a 5- or 6-membered carbocyclic ring optionally substituted with methyl, halo or —$CF_3$;
Ring A is phenyl, naphthyl, a 5- or 6-membered heteroaryl ring containing at least one heteroatom selected from the group consisting of N, O and S; or a 10- or 11-membered fused heteroaryl ring containing at least one heteroatom selected from the group consisting of N, O and S;

$R^4$ is selected from $C_1$-$C_4$alkyl, halo, cyano or —$CF_3$;

m is the integer 0, 1 or 2;

n is the integer 0, 1, 2 or 3; and when n is the integer 2 or 3 then each $R^4$ can be the same or different; and pharmaceutically acceptable salts thereof.

In one aspect of the invention, Ring A is selected from the group consisting of phenyl, naphthyl, quinolinyl, indolyl, indazolyl, furanyl, thiophenyl, pyridinyl, pyrimidinyl, pyrazinyl, pyridazinyl, imidazolyl, pyrazolyl, pyrrolyl, thiazolyl, isoxazolyl, oxazolyl, isothiazolyl, triazolyl or tetrazolyl; each substituted with $(R^4)_n$, wherein n is the integer 0, 1 or 2. In another aspect, Ring A is phenyl, indolyl, thiophenyl, pyridinyl, pyrimidinyl, pyrazinyl, imidazolyl, pyrazolyl, thiazolyl, isothiazolyl or triazolyl; each substituted with $(R^4)_n$ wherein n is the integer 0, 1 or 2. In another aspect, Ring A is phenyl, indolyl, indazolyl, thiophenyl, pyridinyl, pyridazinyl, imidazolyl, thiazolyl or isothiazolyl; each substituted with $(R^4)_n$ wherein n is the integer 0, 1 or 2. In another aspect, Ring A is phenyl, indolyl, indazolyl, thiophenyl, pyridinyl, thiazolyl or isothiazolyl; each substituted with $(R^4)_n$ wherein n is the integer 0, 1 or 2. In another aspect, Ring A is phenyl, indolyl, thiophenyl, pyridinyl, thiazolyl or isothiazolyl; each substituted with $(R^4)_n$ wherein n is the integer 0 or 1. In another aspect, Ring A is phenyl, thiophenyl, isothiazolyl or indolyl, each substituted with $(R^4)_n$ wherein n is the integer 0 or 1. In another aspect, Ring A is phenyl substituted with $(R^4)_n$ wherein n is the integer 0 or 1. In another aspect, Ring A is indolyl substituted with $(R^4)_n$ wherein n is the integer 0 or 1. In another aspect, Ring A is thiophenyl substituted with $(R^4)_n$ wherein n is the integer 0 or 1. In another aspect, Ring A is isothiazolyl substituted with $(R^4)_n$ wherein n is the integer 0 or 1.

In one aspect of the invention, X is CH. In another aspect, X is N.

In one aspect of the invention, L is O. In another aspect, L is $NR^1$. In another aspect, L is $NR^1$ wherein $R^1$ is H; or $R^1$ is phenyl or pyridinyl each optionally substituted with one or two $R^4$ substituents. In another aspect, L is $NR^1$ wherein $R^1$ is H; or $R^1$ is phenyl or pyridinyl each optionally substituted with one $R^4$ substituent. In another aspect, L is $NR^1$ wherein $R^1$ is H; or $R^1$ is pyridinyl or phenyl each optionally substituted with fluoro, chloro or —$CF_3$. In another aspect, L is $NR^1$ wherein $R^1$ is H; or $R^1$ is phenyl optionally substituted with fluoro, chloro or —$CF_3$. In another aspect, L is $NR^1$ wherein $R^1$ is H; or $R^1$ is phenyl optionally substituted with fluoro. In another aspect, L is $NR^1$ wherein $R^1$ is H.

In one aspect of the invention, X' is N. In another aspect, X' is $CR^2$ and $R^2$ is H, methyl, halo or —$CF_3$. In another aspect, X' is $CR^2$ and $R^2$ is H, methyl, fluoro, chloro or —$CF_3$. In another aspect, X' is $CR^2$ and $R^2$ is H, methyl or —$CF_3$. In another aspect, X' is $CR^2$ and $R^2$ is H, or X' is CH.

In one aspect of the invention, $R^3$ is H, methyl, ethyl, isopropyl, fluoro, chloro, —$CF_3$ or cyano. In another aspect, $R^3$ is H, methyl, fluoro, chloro, —$CF_3$ or cyano.

In another aspect, $R^3$ is H, methyl, fluoro, chloro or cyano. In another aspect, $R^3$ is H, methyl, chloro or cyano. In another aspect, $R^3$ is H or cyano. In another aspect, $R^3$ is H.

In one aspect of the invention, $R^2$ and $R^3$ join together to form a fused cyclopentyl or cyclohexyl ring optionally substituted with halo or —$CF_3$. In another aspect, $R^2$ and $R^3$ join together to form a fused cyclopentyl or cyclohexyl ring optionally substituted with fluoro, chloro or —$CF_3$. In another aspect, $R^2$ and $R^3$ join together to form a fused cyclopentyl or cyclohexyl ring optionally substituted with fluoro or chloro. In another aspect, $R^2$ and $R^3$ join together to form a fused cyclopentyl or cyclohexyl ring. In another aspect, $R^2$ and $R^3$ join together to form a fused cyclohexyl ring.

In one aspect of the invention, $R^4$ is methyl, ethyl, propyl, isopropyl, butyl, t-butyl, chloro, fluoro, bromo, iodo, cyano or —$CF_3$. In another aspect of the invention; $R^4$ is methyl, ethyl, propyl, isopropyl, chloro, fluoro, bromo, cyano or —$CF_3$. In another aspect of the invention; $R^4$ is methyl, ethyl, isopropyl, chloro, fluoro, cyano or —$CF_3$. In another aspect of the invention; $R^4$ is methyl, chloro, fluoro or —$CF_3$.

In one aspect of the invention, m is the integer 0 or 1. In another aspect, m is the integer 0. In another aspect of the invention, m is the integer 1.

In one aspect of the invention, n is the integer 0, 1 or 2; and when n is the integer 2, then each $R^4$ can be the same or different. In another aspect, n is the integer 0 or 1. In another aspect, n is the integer 1. In another aspect, n is the integer 0.

In one aspect of the invention, is a Formula (1) compound wherein Ring A is phenyl; m is the integer 1 and n is the integer 0, 1 or 2; X is CH, L is $NR^1$ and $R^1$ is H; X' is $CR^2$ and $R^2$ and $R^3$ join together to form cyclopentyl or cyclohexyl; and $R^4$ is fluoro, chloro or —$CF_3$. In another aspect, is a Formula (1) compound wherein Ring A is phenyl; m is the integer 1 and n is the integer 0 or 1; X is CH; L is $NR^1$ and $R^1$ is H; X' is $CR^2$ and $R^2$ and $R^3$ join together to form cyclohexyl; and $R^4$ is fluoro, chloro or —$CF_3$; or pharmaceutically acceptable salts thereof. In another aspect, is a Formula (1) compound wherein Ring A is phenyl; m is the integer 1 and n is the integer 0; X is CH; L is $NR^1$ and $R^1$ is H; X' is $CR^2$ and $R^2$ and $R^3$ join together to form cyclohexyl; and pharmaceutically acceptable salts thereof.

In one aspect of the invention, is a Formula (1) compound wherein X is CH; L is $NR^1$ wherein $R^1$ is H; or $R^1$ is phenyl or pyridinyl each optionally substituted with one or two $R^4$ substituents; Ring A is phenyl, naphthyl, quinolinyl, indolyl, furanyl, thiophenyl, pyridinyl, pyrimidinyl, pyrazinyl, pyridazinyl, indazolyl, imidazolyl, pyrazolyl, pyrrolyl, thiazolyl, isoxazolyl, oxazolyl, isothiazolyl, triazolyl or tetrazolyl, each substituted with $(R^4)_n$; X' is $CR^2$ wherein $R^2$ is H, methyl or —$CF_3$; $R^3$ is H or cyano; m is the integer 1 and n is the integer 0, 1 or 2; and pharmaceutically acceptable salts thereof. In another aspect, is a Formula (1) compound wherein X is CH; L is $NR^1$ wherein $R^1$ is H; or $R^1$ is phenyl or pyridinyl each optionally substituted with one or two $R^4$ substituents; Ring A is phenyl, indolyl, indazolyl, thiophenyl, pyridinyl, pyrimidinyl, pyrazinyl, imidazolyl, pyrazolyl, thiazolyl, isothiazolyl or triazolyl, each substituted with $(R^4)_n$; X' is $CR^2$ wherein $R^2$ is H, methyl or —$CF_3$; $R^3$ is H or cyano; m is the integer 1 and n is the integer 0, 1 or 2; and pharmaceutically acceptable salts thereof. In another aspect, is a Formula (1) compound wherein X is CH; L is $NR^1$ wherein $R^1$ is H; or $R^1$ is phenyl or pyridinyl each optionally substituted with one $R^4$ substituent; Ring A is phenyl, indolyl, indazolyl, thiophenyl, pyridinyl, imidazolyl, thiazolyl or isothiazolyl, each substituted with $(R^4)_n$; X' is $CR^2$ wherein $R^2$ is H, methyl or —$CF_3$; $R^3$ is H or cyano; m is the integer 1 and n is the integer 0, 1 or 2; and pharmaceutically acceptable salts thereof. In another aspect, is a Formula (1) compound wherein X is CH; L is $NR^1$ wherein $R^1$ is H; or $R^1$ is phenyl optionally substituted with one $R^4$ substituent; Ring A is phenyl, indolyl, thiophenyl, pyridinyl, thiazolyl or isothiazolyl, each substituted with $(R^4)_n$; X' is $CR^2$ wherein $R^2$ is H, methyl or —$CF_3$; $R^3$ is H or cyano; m is the integer 1 and n is the integer 0, 1 or 2; and pharmaceutically acceptable salts thereof. In another aspect, is a Formula (1) compound wherein X is CH; L is NR$^1$ wherein R$^1$ is H; or R$^1$ is phenyl optionally substituted with fluoro; Ring A is phenyl, indolyl, thiophenyl, pyridinyl, thiazolyl or isothiazolyl, each substituted with (R$^4$)$_n$; X' is CR$^2$ wherein R$^2$ is H, methyl or —CF$_3$; R$^3$ is H or cyano; m is the integer 1 and n is the integer 0 or 1; and pharmaceutically acceptable salts thereof. In another aspect, is a Formula (1) compound wherein X is CH; L is NR$^1$ wherein R$^1$ is H; or R$^1$ is phenyl optionally substituted with fluoro; Ring A is phenyl, indolyl, thiophenyl, thiazolyl or isothiazolyl, each substituted with (R$^4$)$_n$; X' is CR$^2$ wherein R$^2$ is H, methyl or —CF$_3$; R$^3$ is H; m is the integer 1 and n is the integer 0 or 1; and pharmaceutically acceptable salts thereof. In another aspect, is a Formula (1) compound wherein X is CH; L is NR$^1$ wherein R$^1$ is H; Ring A is phenyl, indolyl, thiophenyl or isothiazolyl, each substituted with (R$^4$)$_n$; X' is CR$^2$ wherein R$^2$ is H, methyl or —CF$_3$; R$^3$ is H; m is the integer 1 and n is the integer 0 or 1; and pharmaceutically acceptable salts thereof.

In another aspect of the invention, is a Formula (1) compound wherein X is CH; L is O; Ring A is phenyl substituted with (R$^4$)$_n$; X' is CR$^2$; R$^2$ and R$^3$ are both H; m is the integer 1; and n is the integer 0, 1 or 2; and pharmaceutically acceptable salts thereof. In another aspect, is a Formula (1) compound wherein X is CH; L is O; Ring A is phenyl substituted with (R$^4$)$_n$; X' is CR$^2$; R$^2$ and R$^3$ are both H; m is the integer 1; and n is the integer 0 or 1; and pharmaceutically acceptable salts thereof. In another aspect, is a Formula (1) compound wherein X is CH; L is O; Ring A is phenyl substituted with (R$^4$)$_n$; X' is CR$^2$; R$^2$ and R$^3$ are both H; R$^4$ is methyl, fluoro, chloro or —CF$_3$; m is the integer 1; and n is the integer 0 or 1; and pharmaceutically acceptable salts thereof. In another aspect, is a Formula (1) compound wherein X is CH; L is O; Ring A is phenyl substituted with (R$^4$)$_n$; X' is CR$^2$; R$^2$ and R$^3$ are both H; R$^4$ is methyl, fluoro or chloro; m is the integer 1; and n is the integer 0 or 1; and pharmaceutically acceptable salts thereof.

In another aspect of the invention, is a Formula (1) compound wherein X is CH; L is O or NR$^1$; Ring A is phenyl, pyridinyl, indolyl, thiophenyl, isothiazolyl or thiazolyl, each substituted with (R$^4$)$_n$; X' is CR$^2$; R$^1$, R$^2$ and R$^3$ are each H; m is the integer 1; and n is the integer 0, 1 or 2; and pharmaceutically acceptable salts thereof. In another aspect, is a Formula (1) compound wherein X is CH; L is O or NR$^1$; Ring A is phenyl, pyridinyl, indolyl, thiophenyl, isothiazolyl or thiazolyl; each substituted with (R$^4$)$_n$; X' is CR$^2$; R$^1$, R$^2$ and R$^3$ are each H; m is the integer 1; and n is the integer 0, 1 or 2; and pharmaceutically acceptable salts thereof. In another aspect, is a Formula (1) compound wherein X is CH; L is O or NR$^1$; Ring A is phenyl, indolyl, thiophenyl, isothiazolyl or thiazolyl; each substituted with (R$^4$)$_n$; X' is CR$^2$; R$^1$, R$^2$ and R$^3$ are each H; m is the integer 1; and n is the integer 0 or 1; and pharmaceutically acceptable salts thereof. In another aspect, is a Formula (1) compound wherein X is CH; L is O or NR$^1$; Ring A is phenyl, indolyl, thiophenyl or isothiazolyl; each substituted with (R$^4$)$_n$; X' is CR$^2$; R$^1$, R$^2$ and R$^3$ are each H; R$^4$ is methyl, fluoro, chloro or —CF$_3$; m is the integer 1; and n is the integer 0 or 1; and pharmaceutically acceptable salts thereof.

In another aspect of the invention, is a Formula (1) compound wherein X is CH or N; L is NR$^1$; Ring A is phenyl, pyridinyl, indolyl, thiophenyl, isothiazolyl or thiazolyl, each substituted with (R$^4$)$_n$; X' is CR$^2$; R$^1$, R$^2$ and R$^3$ are each H; m is the integer 1 and n is the integer 0, 1 or 2; and pharmaceutically acceptable salts thereof. In another aspect, is a Formula (1) compound wherein X is CH or N; L is NR$^1$; Ring A is phenyl, pyridinyl, indolyl, thiophenyl, isothiazolyl or thiazolyl, each substituted with (R$^4$)$_n$; X' is CR$^2$; R$^1$, R$^2$ and R$^3$ are each H; R$^4$ is methyl, fluoro, chloro or —CF$_3$; m is the integer 1 and n is the integer 0, 1 or 2; and pharmaceutically acceptable salts thereof. In another aspect, is a Formula (1) compound wherein X is CH or N; L is NR$^1$; Ring A is phenyl, indolyl, pyridinyl, thiophenyl or isothiazolyl, each substituted with (R$^4$)$_n$; X' is CR$^2$; R$^1$, R$^2$ and R$^3$ are each H; R$^4$ is methyl, fluoro or chloro; m is the integer 1 and n is the integer 0, 1 or 2; and pharmaceutically acceptable salts thereof. In another aspect, is a Formula (1) compound wherein X is CH or N; L is NR$^1$; Ring A is phenyl substituted with (R$^4$)$_n$; X' is CR$^2$; R$^1$, R$^2$ and R$^3$ are each H; R$^4$ is fluoro or chloro; m is the integer 1 and n is the integer 0 or 1; and pharmaceutically acceptable salts thereof.

In another aspect of the invention, is a Formula (1) compound wherein Ring A is phenyl, indolyl, pyridinyl, thiophenyl or isothiazolyl; X is N; L is NR$^1$; X' is CR$^2$; R$^1$, R$^2$ and R$^3$ are each H; R$^4$ is methyl, fluoro, chloro or —CF$_3$; m is the integer 1, and n is the integer 0, 1 or 2; and pharmaceutically acceptable salts thereof. In another aspect, is a Formula (1) compound wherein Ring A is phenyl, indolyl, pyridinyl, thiophenyl or isothiazolyl; X is N; L is NR$^1$; X' is CR$^2$; R$^1$, R$^2$ and R$^3$ are each H; R$^4$ is fluoro or chloro; m is the integer 1, and n is the integer 0, 1 or 2; and pharmaceutically acceptable salts thereof. In another aspect, is a Formula (1) compound wherein Ring A is phenyl, indolyl, pyridinyl, thiophenyl or isothiazolyl; X is N; L is NR$^1$; X' is CR$^2$; R$^1$, R$^2$ and R$^3$ are each H; R$^4$ is fluoro or chloro; m is the integer 1, and n is the integer 0 or 1; or pharmaceutically acceptable salts thereof.

In another aspect of the invention, is a Formula (1) compound wherein Ring A is phenyl, indolyl, pyridinyl, thiophenyl or isothiazolyl; X is CH or N; L is NR$^1$ or O; and wherein R$^1$ is H; X' is CR$^2$ wherein R$^2$ is H or methyl; R$^3$ is H or cyano; R$^4$ is fluoro, chloro or —CF$_3$; m is the integer 1, and n is the integer 0, 1 or 2; and pharmaceutically acceptable salts thereof. In another aspect, is a Formula (1) compound wherein Ring A is phenyl, indolyl, pyridinyl, thiophenyl or isothiazolyl; X is CH or N; L is NR$^1$ or O; X' is CR$^2$; R$^1$, R$^2$ and R$^3$ are each H; R$^4$ is fluoro or chloro; m is the integer 1, and n is the integer 0, 1 or 2; and pharmaceutically acceptable salts thereof. In another aspect, is a Formula (1) compound wherein Ring A is phenyl, indolyl, pyridinyl, thiophenyl or isothiazolyl; X is CH or N; L is NR$^1$ or O; X' is CR$^2$; R$^1$, R$^2$ and R$^3$ are each H; R$^4$ is fluoro or chloro; m is the integer 1, and n is the integer 0 or 1; and pharmaceutically acceptable salts thereof.

In another aspect of the invention, is a Formula (1) compound selected from the group consisting of:
N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-((1H-indol-5-yl)methyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;

N-((1R,3s,5S)-8-benzyl-8-azabicyclo[3.2.1]octan-3-yl)-2,3, 4,9-tetrahydro-1H-carbazole-7-carboxamide;
N-((1R,3s,5S)-8-benzyl-8-azabicyclo[3.2.1]octan-3-yl)-1H-indazole-6-carboxamide;
N-((1R,3s,5S)-8-(4-(trifluoromethyl)benzyl)-8-azabicyclo [3.2.1]octan-3-yl)-1H-indole-6-carboxamide;
N-((1R,3s,5S)-8-(pyridin-2-ylmethyl)-8-azabicyclo[3.2.1] octan-3-yl)-1H-indole-6-carboxamide;
N-((1R,3s,5S)-8-(pyridin-3-ylmethyl)-8-azabicyclo[3.2.1] octan-3-yl)-1H-indole-6-carboxamide;
N-((1R,3s,5S)-8-(pyridin-4-ylmethyl)-8-azabicyclo[3.2.1] octan-3-yl)-1H-indole-6-carboxamide;
N-((1R,3s,5S)-8-(pyrazin-2-ylmethyl)-8-azabicyclo[3.2.1] octan-3-yl)-1H-indole-6-carboxamide;
N-((1R,3s,5S)-8-((1-methyl-1H-imidazol-2-yl)methyl)-8-azabicyclo[3.2.1]octan-3-yl)-1H-indole-6-carboxamide;
N-((1R,3s,5S)-8-phenyl-8-azabicyclo[3.2.1]octan-3-yl)-1H-indole-6-carboxamide;
N-((1R,3s,5S)-8-benzyl-8-azabicyclo[3.2.1]octan-3-yl)-1-(pyridin-4-yl)-1H-indole-6-carboxamide;
N-((1R,3s,5S)-8-benzyl-8-azabicyclo[3.2.1]octan-3-yl)-3-cyano-1H-indole-6-carboxamide;
N-((1R,3s,5S)-8-benzyl-8-azabicyclo[3.2.1]octan-3-yl)-2-(trifluoromethyl)-1H-indole-6-carboxamide;
N-((1R,3s,5S)-8-benzyl-8-azabicyclo[3.2.1]octan-3-yl)-1-(4-(trifluoromethyl)phenyl)-1H-indole-6-carboxamide;
N-((1R,3s,5S)-8-benzyl-8-azabicyclo[3.2.1]octan-3-yl)-1-(4-fluorophenyl)-1H-indole-6-carboxamide;
N-((1R,3s,5S)-8-benzyl-8-azabicyclo[3.2.1]octan-3-yl)-1-phenyl-1H-indole-6-carboxamide;
N-((1R,3s,5S)-8-benzyl-8-azabicyclo[3.2.1]octan-3-yl)benzofuran-6-carboxamide;
N-((1R,3s,5S)-8-(isothiazol-5-ylmethyl)-8-azabicyclo [3.2.1]octan-3-yl)-1H-indole-6-carboxamide;
N-((1R,3s,5S)-8-(isothiazol-3-ylmethyl)-8-azabicyclo [3.2.1]octan-3-yl)-1H-indole-6-carboxamide;
N-((1R,3s,5S)-8-(thiazol-2-ylmethyl)-8-azabicyclo[3.2.1] octan-3-yl)-1H-indole-6-carboxamide; and
N-((1R,3s,5S)-8-((4-methylthiazol-2-yl)methyl)-8-azabicyclo[3.2.1]octan-3-yl)-1H-indole-6-carboxamide; and pharmaceutically acceptable salts thereof.

In another aspect of the invention, is a Formula (1) compound with a c5-HT2B inhibitory $IC_{50}$ of <1000 nM selected from the group consisting of:
N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-((1H-indol-5-yl)methyl)-8-azabicyclo [3.2.1]octan-3-yl)-1H-indole-6-carboxamide;
N-((1R,3s,5S)-8-(thiophen-2-ylmethyl)-8-azabicyclo[3.2.1] octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-benzyl-8-azabicyclo[3.2.1]octan-3-yl)-2,3, 4,9-tetrahydro-1H-carbazole-7-carboxamide;
N-((1R,3s,5S)-8-benzyl-8-azabicyclo[3.2.1]octan-3-yl)-1H-indazole-6-carboxamide;
N-((1R,3s,5S)-8-(4-(trifluoromethyl)benzyl)-8-azabicyclo [3.2.1]octan-3-yl)-1H-indole-6-carboxamide;
N-((1R,3s,5S)-8-(pyridin-2-ylmethyl)-8-azabicyclo[3.2.1] octan-3-yl)-1H-indole-6-carboxamide;
N-((1R,3s,5S)-8-(pyridin-3-ylmethyl)-8-azabicyclo[3.2.1] octan-3-yl)-1H-indole-6-carboxamide;
N-((1R,3s,5S)-8-benzyl-8-azabicyclo[3.2.1]octan-3-yl)-1-(pyridin-4-yl)-1H-indole-6-carboxamide;
N-((1R,3s,5S)-8-benzyl-8-azabicyclo[3.2.1]octan-3-yl)-3-cyano-1H-indole-6-carboxamide;
N-((1R,3s,5S)-8-benzyl-8-azabicyclo[3.2.1]octan-3-yl)-2-(trifluoromethyl)-1H-indole-6-carboxamide;
N-((1R,3s,5S)-8-benzyl-8-azabicyclo[3.2.1]octan-3-yl)-1-(4-fluorophenyl)-1H-indole-6-carboxamide;
N-((1R,3s,5S)-8-benzyl-8-azabicyclo[3.2.1]octan-3-yl)-1-phenyl-1H-indole-6-carboxamide;
N-((1R,3s,5S)-8-benzyl-8-azabicyclo[3.2.1]octan-3-yl)benzofuran-6-carboxamide;
N-((1R,3s,5S)-8-(isothiazol-5-ylmethyl)-8-azabicyclo [3.2.1]octan-3-yl)-1H-indole-6-carboxamide;
N-((1R,3s,5S)-8-(isothiazol-3-ylmethyl)-8-azabicyclo [3.2.1]octan-3-yl)-1H-indole-6-carboxamide;

N-((1R,3s,5S)-8-(thiazol-2-ylmethyl)-8-azabicyclo[3.2.1]octan-3-yl)-1H-indole-6-carboxamide; and
N-((1R,3s,5S)-8-((4-methylthiazol-2-yl)methyl)-8-azabicyclo[3.2.1]octan-3-yl)-1H-indole-6-carboxamide; and pharmaceutically acceptable salts thereof.

In another aspect of the invention, is a Formula (1) compound with a c5-HT2B inhibitory $IC_{50}$ of <100 nM selected from the group consisting of:
N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-((1H-indol-5-yl)methyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-(4-(trifluoromethyl)benzyl)-8-azabicyclo[3.2.1]octan-3-yl)-1H-indole-6-carboxamide;
N-((1R,3s,5S)-8-(pyridin-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-(trifluoromethyl)-1H-indole-6-carboxamide;
N-((1R,3s,5S)-8-benzyl-8-azabicyclo[3.2.1]octan-3-yl)-1-(4-fluorophenyl)-1H-indole-6-carboxamide;
N-((1R,3s,5S)-8-benzyl-8-azabicyclo[3.2.1]octan-3-yl)-1-phenyl-1H-indole-6-carboxamide;
N-((1R,3s,5S)-8-benzyl-8-azabicyclo[3.2.1]octan-3-yl)benzofuran-6-carboxamide;
N-((1R,3s,5S)-8-(isothiazol-5-ylmethyl)-8-azabicyclo[3.2.1]octan-3-yl)-1H-indole-6-carboxamide; and
N-((1R,3s,5S)-8-(isothiazol-3-ylmethyl)-8-azabicyclo[3.2.1]octan-3-yl)-1H-indole-6-carboxamide; and pharmaceutically acceptable salts thereof.

In another aspect of the invention, is a Formula (1) compound with a c5-HT2B inhibitory $IC_{50}$ of <10 nM selected from the group consisting of:
N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-((1H-indol-5-yl)methyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-benzyl-8-azabicyclo[3.2.1]octan-3-yl)benzofuran-6-carboxamide; and
N-((1R,3s,5S)-8-(isothiazol-5-ylmethyl)-8-azabicyclo[3.2.1]octan-3-yl)-1H-indole-6-carboxamide; and pharmaceutically acceptable salts thereof.

In another aspect of the invention, is a Formula (1) compound with a c5-HT2B inhibitory $IC_{50}$ of <1 nM selected from the group consisting of:
N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-((1H-indol-5-yl)methyl)-8-azabicyclo[3.2.1]octan-3-yl)-1H-indole-6-carboxamide; and
N-((1R,3s,5S)-8-benzyl-8-azabicyclo[3.2.1]octan-3-yl)benzofuran-6-carboxamide; and
pharmaceutically acceptable salts thereof.

In another aspect of the invention, is a Formula (1) compound with a c5-HT2B inhibitory $IC_{50}$ of <1 nM that is N-((1R,3s,5S)-8-benzyl-8-azabicyclo[3.2.1]octan-3-yl)-1H-indole-6-carboxamide; or a pharmaceutically acceptable salt thereof.

In another aspect of the invention, is a Formula (1) compound with a c5-HT2B inhibitory $IC_{50}$ of <1 nM that is N-((1R,3s,5S)-8-benzyl-8-azabicyclo[3.2.1]octan-3-yl)-1H-pyrrolo[2,3-b]pyridine-6-carboxamide; or a pharmaceutically acceptable salt thereof.

In another aspect of the invention, is a Formula (1) compound with a c5-HT2B inhibitory $IC_{50}$ of <1 nM that is N-((1R,3s,5S)-8-(4-fluorobenzyl)-8-azabicyclo[3.2.1]octan-3-yl)-1H-indole-6-carboxamide; or a pharmaceutically acceptable salt thereof.

In another aspect of the invention, is a Formula (1) compound with a c5-HT2B inhibitory $IC_{50}$ of <1 nM that is N-((1R,3s,5S)-8-(4-chlorobenzyl)-8-azabicyclo[3.2.1]octan-3-yl)-1H-indole-6-carboxamide; or a pharmaceutically acceptable salt thereof.

In another aspect of the invention, is a Formula (1) compound with a c5-HT2B inhibitory $IC_{50}$ of <1 nM that is N-((1R,3s,5S)-8-((1H-indol-5-yl)methyl)-8-azabicyclo[3.2.1]octan-3-yl)-1H-indole-6-carboxamide; or a pharmaceutically acceptable salt thereof.

In another aspect of the invention, is a Formula (1) compound with a c5-HT2B inhibitory $IC_{50}$ of <1 nM that is N-((1R,3s,5S)-8-benzyl-8-azabicyclo[3.2.1]octan-3-yl)benzofuran-6-carboxamide; or a pharmaceutically acceptable salt thereof.

In another aspect, is a Formula (1) compound that is a Formula (1A) compound,

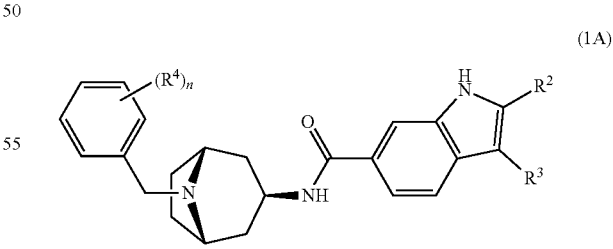

(1A)

and pharmaceutically acceptable salts thereof, wherein $R^2$, $R^3$ and $(R^4)_n$ are as defined herein. In another aspect, is a Formula (1A) compound wherein $R^2$, $R^3$ and $R^4$ are as defined herein and n is the integer 0, 1 or 2; and pharmaceutically acceptable salts thereof. In another aspect, is a Formula (1A) compound wherein $R^2$ is H, methyl, fluoro chloro or —$CF_3$; $R^3$ is H, fluoro, chloro, methyl or cyano; $R^4$ is methyl, halo or —CF$_3$; and n is the integer 0, 1 or 2; and pharmaceutically acceptable salts thereof. In another aspect, is a Formula (1A) compound wherein R$^2$ is H, methyl or —CF$_3$; R$^3$ is H or cyano; R$^4$ wherein R$^4$ is methyl, fluoro, chloro or —CF$_3$; and n is the integer 0, 1 or 2; and pharmaceutically acceptable salts thereof. In another aspect, is a Formula (1A) compound wherein R$^2$ and R$^3$ are both H; R$^4$ is fluoro, chloro or —CF$_3$; and n is the integer 0 or 1; and pharmaceutically acceptable salts thereof.

In another aspect, is a Formula (1A) compound selected from the group consisting of:
N-((1R,3s,5S)-8-benzyl-8-azabicyclo[3.2.1]octan-3-yl)-1H-indole-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-(4-(trifluoromethyl)benzyl)-8-azabicyclo[3.2.1]octan-3-yl)-1H-indole-6-carboxamide;
N-((1R,3s,5S)-8-benzyl-8-azabicyclo[3.2.1]octan-3-yl)-3-cyano-1H-indole-6-carboxamide; and
N-((1R,3s,5S)-8-benzyl-8-azabicyclo[3.2.1]octan-3-yl)-2-(trifluoromethyl)-1H-indole-6-carboxamide; and pharmaceutically acceptable salts thereof.

In another aspect, is a Formula (1A) compound with a c5-HT2B IC$_{50}$<100 nM selected from the group consisting of:
N-((1R,3s,5S)-8-benzyl-8-azabicyclo[3.2.1]octan-3-yl)-1H-indole-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-(4-(trifluoromethyl)benzyl)-8-azabicyclo[3.2.1]octan-3-yl)-1H-indole-6-carboxamide; and
N-((1R,3s,5S)-8-benzyl-8-azabicyclo[3.2.1]octan-3-yl)-2-(trifluoromethyl)-1H-indole-6-carboxamide; and pharmaceutically acceptable salts thereof.

In another aspect, is a Formula (1A) compound with a c5-HT2B IC$_{50}$<10 nM selected from the group consisting of:
N-((1R,3s,5S)-8-benzyl-8-azabicyclo[3.2.1]octan-3-yl)-1H-indole-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide; and
N-((1R,3s,5S)-8-benzyl-8-azabicyclo[3.2.1]octan-3-yl)-2-methyl-1H-indole-6-carboxamide; and pharmaceutically acceptable salts thereof.

In another aspect, is a Formula (1A) compound with a c5-HT2B IC$_{50}$<1 nM selected from the group consisting of:
N-((1R,3s,5S)-8-benzyl-8-azabicyclo[3.2.1]octan-3-yl)-1H-indole-6-carboxamide;
N-((1R,3s,5S)-8-(4-fluorobenzyl)-8-azabicyclo[3.2.1]octan-3-yl)-1H-indole-6-carboxamide; and
N-((1R,3s,5S)-8-(4-chlorobenzyl)-8-azabicyclo[3.2.1]octan-3-yl)-1H-indole-6-carboxamide; and pharmaceutically acceptable salts thereof.

In another aspect of the invention, is a Formula (1) compound that is a Formula

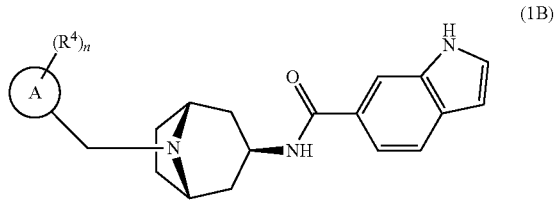

(1B) compound wherein Ring A is indolyl, thiophenyl, pyridinyl, pyrazinyl, isothiazolyl or thiazolyl, each substituted with (R$^4$)$_n$; wherein (R$^4$)$_n$ is as defined herein; and pharmaceutically acceptable salts thereof. In another aspect, is a Formula (1B) compound wherein Ring A is indolyl, thiophenyl, pyridinyl, isothiazolyl or thiazolyl, each substituted with (R$^4$)$_n$; wherein R$^4$ is methyl, halo or —CF$_3$; and n is the integer 0, 1 or 2; and pharmaceutically acceptable salts thereof. In another aspect, is a Formula (1B) compound wherein Ring A is indolyl, thiophenyl, pyridinyl, isothiazolyl or thiazolyl, each substituted with (R$^4$)$_n$; wherein R$^4$ is methyl, fluoro, chloro or —CF$_3$; and n is the integer 0, 1 or 2; and pharmaceutically acceptable salts thereof. In another aspect, is a Formula (1B) compound wherein Ring A is indolyl, thiophenyl, isothiazolyl or thiazolyl, each substituted with (R$^4$)$_n$; wherein R$^4$ is methyl, fluoro, chloro or —CF$_3$; and n is the integer 0 or 1; and pharmaceutically acceptable salts thereof. In another aspect, is a Formula (1B) compound selected from the group consisting of:
N-((1R,3s,5S)-8-((1H-indol-5-yl)methyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-(pyridin-2-ylmethyl)-8-azabicyclo[3.2.1]octan-3-yl)-1H-indole-6-carboxamide;
N-((1R,3s,5S)-8-(pyridin-3-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-1-phenyl-1H-indole-6-carboxamide;
N-((1R,3s,5S)-8-(isothiazol-5-ylmethyl)-8-azabicyclo[3.2.1]octan-3-yl)-1H-indole-6-carboxamide;
N-((1R,3s,5S)-8-(isothiazol-3-ylmethyl)-8-azabicyclo[3.2.1]octan-3-yl)-1H-indole-6-carboxamide;
N-((1R,3s,5S)-8-(thiazol-2-ylmethyl)-8-azabicyclo[3.2.1]octan-3-yl)-1H-indole-6-carboxamide; and
N-((1R,3s,5S)-8-((4-methylthiazol-2-yl)methyl)-8-azabicyclo[3.2.1]octan-3-yl)-1H-indole-6-carboxamide; and pharmaceutically acceptable salts thereof.

In another aspect, is a Formula (1B) compound with a c5-5HT2B IC50<100 nM selected from the group consisting of:
N-((1R,3s,5S)-8-((1H-indol-5-yl)methyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-(pyridin-2-ylmethyl)-8-azabicyclo[3.2.1]octan-3-yl)-1H-indole-6-carboxamide;
N-((1R,3s,5S)-8-(isothiazol-5-ylmethyl)-8-azabicyclo[3.2.1]octan-3-yl)-1H-indole-6-carboxamide; and
N-((1R,3s,5S)-8-(isothiazol-3-ylmethyl)-8-azabicyclo[3.2.1]octan-3-yl)-1H-indole-6-carboxamide; and pharmaceutically acceptable salts thereof.

In another aspect, is a Formula (1B) compound with a c5-5HT2B IC50<10 nM selected from the group consisting of:

N-((1R,3s,5S)-8-((1H-indol-5-yl)methyl)-8-azabicyclo
[3.2.1]octan-3-yl)-1H-indole-6-carboxamide;

N-((1R,3s,5S)-8-(thiophen-2-ylmethyl)-8-azabicyclo[3.2.1]
octan-3-yl)-1H-indole-6-carboxamide; and N-((1R,3s,5S)-8-(isothiazol-5-ylmethyl)-8-azabicyclo
[3.2.1]octan-3-yl)-1H-indole-6-carboxamide; and pharmaceutically acceptable salts thereof.

In another aspect, is a Formula (1B) compound with a c5-5HT2B IC50<1 nM that is N-((1R,3s,5S)-8-((1H-indol-5-yl)methyl)-8-azabicyclo[3.2.1]octan-3-yl)-1H-indole-6-carboxamide; and a pharmaceutically acceptable salt thereof.

In another aspect, is a Formula (1) compound that is a Formula (1C) compound,

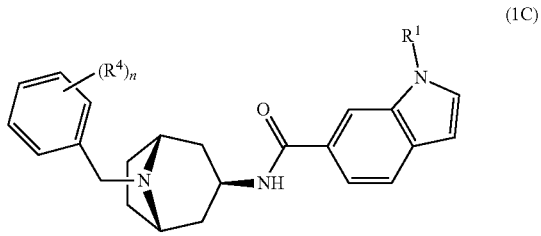

(1C)

wherein $R^1$ is phenyl or pyridinyl; each optionally substituted with fluoro, chloro or —$CF_3$; and $(R^4)_n$ is as defined herein; and pharmaceutically acceptable salts thereof. In another aspect, is a Formula (1C) compound wherein $R^1$ is phenyl or pyridinyl; each optionally substituted with fluoro, chloro or —$CF_3$; $R^4$ is methyl, fluoro, chloro or —$CF_3$; and n is the integer 0, 1 or 2; and pharmaceutically acceptable salts thereof. In another aspect, is a Formula (1C) compound, wherein $R^1$ is phenyl or pyridinyl; each optionally substituted with fluoro or chloro; $R^4$ is fluoro, chloro or —$CF_3$; and n is the integer 0 or 1; and pharmaceutically acceptable salts thereof. In another aspect, is a Formula (1C) compound wherein $R^1$ is phenyl or pyridinyl; each optionally substituted with fluoro or chloro; and n is the integer 0 or 1; and pharmaceutically acceptable salts thereof. In another aspect, is a Formula (1C) compound selected from the group consisting of:

N-((1R,3s,5S)-8-benzyl-8-azabicyclo[3.2.1]octan-3-yl)-1-(pyridin-4-yl)-1H-indole-6-carboxamide;

N-((1R,3s,5S)-8-benzyl-8-azabicyclo[3.2.1]octan-3-yl)-1-(4-fluorophenyl)-1H-indole-6-carboxamide; and N-((1R,3s,5S)-8-benzyl-8-azabicyclo[3.2.1]octan-3-yl)-1-phenyl-1H-indole-6-carboxamide; and pharmaceutically acceptable salts thereof.

In another aspect, is a Formula (1C) compound with a 5c-5HT2B $IC_{50}$<100 nM that is N-((1R,3s,5S)-8-benzyl-8-azabicyclo[3.2.1]octan-3-yl)-1-(4-fluorophenyl)-1H-indole-6-carboxamide or N-((1R,3s,5S)-8-benzyl-8-azabicyclo[3.2.1]octan-3-yl)-1-phenyl-1H-indole-6-carboxamide; and pharmaceutically acceptable salts thereof.

In another aspect, is a Formula (1) compound that is a Formula (1D) compound,

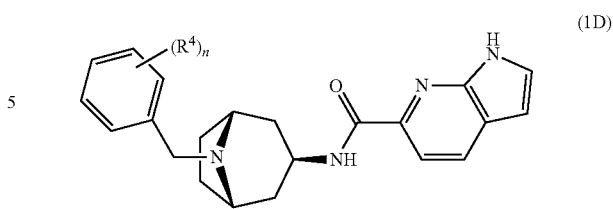

(1D)

wherein $(R^4)_n$ is as defined herein; and pharmaceutically acceptable salts thereof. In another aspect, is a Formula (1D) compound wherein $R^4$ is methyl, halo, or —$CF_3$ and n is the integer 0, 1 or 2; and pharmaceutically acceptable salts thereof. In another aspect, is a Formula (1D) compound wherein $R^4$ is fluoro, chloro or —$CF_3$; and n is the integer 0, 1 or 2; and pharmaceutically acceptable salts thereof. In another aspect, is a Formula (1D) compound wherein $R^4$ is fluoro, chloro or —$CF_3$; and n is the integer 0 or 1; and pharmaceutically acceptable salts thereof. In another aspect, is a Formula (1D) compound wherein $R^4$ is fluoro or chloro; and n is the integer 0 or 1; and pharmaceutically acceptable salts thereof. In another aspect, is a Formula (1D) compound that is N-((1R,3s,5S)-8-benzyl-8-azabicyclo[3.2.1]octan-3-yl)-1H-pyrrolo[2,3-b]pyridine-6-carboxamide or N-((1R,3s,5S)-8-(4-chlorobenzyl)-8-azabicyclo[3.2.1]octan-3-yl)-1H-pyrrolo[2,3-b]pyridine-6-carboxamide; and pharmaceutically acceptable salts thereof.

In another aspect, is a Formula (1D) compound with a 5c-5HT2B IC50<1 nM that is N-((1R,3s,5S)-8-benzyl-8-azabicyclo[3.2.1]octan-3-yl)-1H-pyrrolo[2,3-b]pyridine-6-carboxamide; and a pharmaceutically acceptable salt thereof.

In another aspect, is a Formula (1) compound that is a Formula (1E) compound,

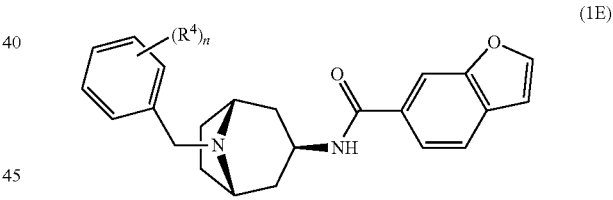

(1E)

wherein $(R^4)_n$ is as defined herein; and pharmaceutically acceptable salts thereof. In another aspect, is a Formula (1E) compound wherein $R^4$ is methyl, halo, or —$CF_3$ and n is the integer 0, 1 or 2; and pharmaceutically acceptable salts thereof. In another aspect, is a Formula (1E) compound wherein $R^4$ is fluoro, chloro or —$CF_3$; and n is the integer 0, 1 or 2; and pharmaceutically acceptable salts thereof. In another aspect, is a Formula (1E) compound wherein $R^4$ is fluoro, chloro or —$CF_3$; and n is the integer 0 or 1; and pharmaceutically acceptable salts thereof. In another aspect, is a Formula (1E) compound wherein $R^4$ is fluoro or chloro; and n is the integer 0 or 1; and pharmaceutically acceptable salts thereof. In another aspect, is a Formula (1E) compound that is N-((1R,3s,5S)-8-benzyl-8-azabicyclo[3.2.1]octan-3-yl)benzofuran-6-carboxamide, and pharmaceutically acceptable salts thereof.

In yet another aspect of the invention, is a composition comprising a Formula (1) compound or a pharmaceutically acceptable salt thereof. In the compositions described below, the Example #'s are interchangeable with each respective compound name as described herein. In another aspect, is a composition comprising a Formula (1) compound that has a c5-5HT2B IC$_{50}$<1000 nM, wherein said compound is any one of Example 1-13, 18-20 or 22-28; or a pharmaceutically acceptable salt thereof. In another aspect, is a composition comprising a Formula (1) compound that has a c5-5HT2B IC$_{50}$<500 nM, wherein said compound is any one of Example 1-12, 19-20 or 22-28; or a pharmaceutically acceptable salt thereof. In another aspect, is a composition comprising a Formula (1) compound that has a c5-5HT2B IC$_{50}$<100 nM, wherein said compound is any one of Example 1-8, 11-12, 20 or 22-26; or a pharmaceutically acceptable salt thereof. In another aspect, is a composition comprising a Formula (1) compound that has a c5-5HT2B IC$_{50}$<10 nM, wherein said compound is any one of Example 1-8, 24 or 25; or a pharmaceutically acceptable salt thereof. In another aspect, is a composition comprising a Formula (1) compound that has a c5-5HT2B IC$_{50}$<1 nM, wherein said compound is any one of Example 1, 2, 4-6 or 24; or a pharmaceutically acceptable salt thereof. In another aspect, the composition comprising a Formula (1) compound, or a pharmaceutically acceptable salt thereof, further comprises at least one pharmaceutically acceptable excipient.

In another aspect, is a composition comprising a Formula (1) compound that is a Formula (1A), Formula (1B), Formula (1C), Formula (1D) or Formula (1E) compound, or a pharmaceutically acceptable salt thereof. In another aspect, is a composition comprising a Formula (1A) compound, or a pharmaceutically acceptable salt thereof. In another aspect, is a composition comprising a Formula (1B) compound, or a pharmaceutically acceptable salt thereof. In another aspect, is a composition comprising a Formula (1C) compound, or a pharmaceutically acceptable salt thereof. In another aspect, is a composition comprising a Formula (1D) compound, or a pharmaceutically acceptable salt thereof. In another aspect, is a composition comprising a Formula (1E) compound, or a pharmaceutically acceptable salt thereof. In another aspect, the composition further comprises at least one pharmaceutically acceptable excipient.

In another aspect, is a composition comprising a Formula (1A) compound with a 5c-5HT2B IC$_{50}$<500 nM, wherein said compound is any one of Example 1, 4-5, 8, 11, 19 or 20; or a pharmaceutically acceptable salt thereof. In another aspect, is a composition comprising a Formula (1A) compound with a 5c-5HT2B IC$_{50}$<100 nM, wherein said compound is any one of Example 1, 4-5, 8, 11 or 20; or a pharmaceutically acceptable salt thereof. In another aspect, is a composition comprising a Formula (1A) compound with a 5c-5HT2B IC$_{50}$<10 nM, wherein said compound is any one of Example 1, 4-5 or 8; or a pharmaceutically acceptable salt thereof. In another aspect, is a composition comprising a Formula (1A) compound with a 5c-5HT2B IC$_{50}$<1 nM, wherein said compound is any one of Example 1, 4 or 5; or a pharmaceutically acceptable salt thereof. In another aspect, the composition further comprises at least one pharmaceutically acceptable excipient.

In another aspect, is a composition comprising a Formula (1B) compound with a 5c-5HT2B IC$_{50}$<1000 nM, wherein said compound is any one of Example 6-7, 12-13, or 25-28; or a pharmaceutically acceptable salt thereof. In another aspect, is a composition comprising a Formula (1B) compound with a 5c-5HT2B IC$_{50}$<500 nM, wherein said compound is any one of Example 6-7, 12 or 25-28; or a pharmaceutically acceptable salt thereof. In another aspect, is a composition comprising a Formula (1B) compound with a 5c-5HT2B IC$_{50}$<100 nM, wherein said compound is any one of Example 6, 7, 12, 25 or 26; or a pharmaceutically acceptable salt thereof. In another aspect, is a composition comprising a Formula (1B) compound with a 5c-5HT2B IC$_{50}$<10 nM, wherein said compound is any one of Example 6, 7 or 25; or a pharmaceutically acceptable salt thereof. In another aspect, is a composition comprising a Formula (1B) compound with a 5c-5HT2B IC$_{50}$<1 nM, wherein said compound is Example 6; or a pharmaceutically acceptable salt thereof. In another aspect, the composition further comprises at least one pharmaceutically acceptable excipient.

In another aspect, is a composition comprising a Formula (1C) compound with a 5c-5HT2B IC$_{50}$<100 nM, wherein said compound is Example 22 or 23; or a pharmaceutically acceptable salt thereof.

In another aspect, is a composition comprising a Formula (1D) compound with a 5c-5HT2B IC$_{50}$<10 nM, wherein said compound is Example 2 or 3; or a pharmaceutically acceptable salt thereof. In another aspect, is a composition comprising a Formula (1D) compound with a 5c-5HT2B IC$_{50}$<1 nM, wherein said compound is Example 2; or a pharmaceutically acceptable salt thereof.

In another aspect, is a composition comprising a Formula (1E) compound with a 5c-5HT2B IC$_{50}$<1 nM, wherein said compound is Example 24; or a pharmaceutically acceptable salt thereof. In another aspect, the composition further comprises at least one pharmaceutically acceptable excipient.

In another aspect, the composition is administered orally or by injection. In another aspect, the composition is administered orally. In another aspect, the composition is administered by subcutaneous injection or intramuscular injection. In another aspect, the composition is administered three times a week. In another aspect, the composition is administered five times a week. In another aspect, the composition is administered every other day. In another aspect, the composition is administered daily. In another aspect, the composition is administered twice daily.

In yet another aspect of the invention, is a method of treating an animal with MMVD, CHF and/or asymptomatic heart failure, by administering a therapeutic amount of a Formula (1) compound, or a pharmaceutically acceptable salt thereof, to the animal in need thereof. In the methods of treatment described below, the Example #'s are interchangeable with each respective compound name as described herein. In another aspect, is a method of treating an animal with MMVD, CHF and/or asymptomatic heart failure, by administering a therapeutic amount of a Formula (1) compound, wherein said compound has a 5c-5HT2B IC$_{50}$<1000 nM and is any one of Example 1-13, 18-20 or 22-28; or a pharmaceutically acceptable salt thereof, to the animal in need thereof. In another aspect, is a method of treating an animal with MMVD, CHF and/or asymptomatic heart failure, by administering a therapeutic amount of a Formula (1) compound, wherein said compound has a 5c-5HT2B IC$_{50}$<500 nM and is any one of Example 1-12, 19-20 or 22-28; or a pharmaceutically acceptable salt thereof, to the animal in need thereof. In another aspect, is a method of treating an animal with MMVD, CHF and/or asymptomatic heart failure, by administering a therapeutic amount of a Formula (1) compound, wherein said compound has a 5c-5HT2B IC$_{50}$<100 nM and is any one of Example 1-8, 11-12, 20 or 22-26; or a pharmaceutically acceptable salt thereof, to the animal in need thereof. In another aspect, is a method of treating an animal with MMVD, CHF and/or asymptomatic heart failure, by administering a therapeutic amount of a Formula (1) compound, wherein said compound has a 5c-5HT2B IC$_{50}$<10 nM and is any one of Example 1-8, 24 or 25; or a pharmaceutically acceptable salt thereof, to the animal in need thereof. In another aspect, is a method of treating an animal with MMVD, CHF and/or asymptomatic heart failure, by administering a therapeutic amount of a Formula (1) compound, wherein said compound has a 5c-5HT2B $IC_{50}$<1 nM and is any one of Example 1, 2, 4-6 or 24; or a pharmaceutically acceptable salt thereof, to the animal in need thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1) compound that is a Formula (1A), Formula (1B), Formula (1C), Formula (1D) or Formula (1E) compound, or a pharmaceutically acceptable salt thereof, to the animal in need thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1A) compound; or a pharmaceutically acceptable salt thereof, to the animal in need thereof. In another aspect, is a method of treating an animal with MMVD, CHF and/or asymptomatic heart failure, by administering a therapeutic amount of a Formula (1A) compound with a 5c-5HT2B $IC_{50}$<500 nM that is any one of Example 1, 4, 5, 8, 11, 19 or 20; or a pharmaceutically acceptable salt thereof, to the animal in need thereof. In another aspect, is a method of treating an animal with MMVD, CHF and/or asymptomatic heart failure, by administering a therapeutic amount of a Formula (1A) compound with a 5c-5HT2B $IC_{50}$<100 nM that is any one of Example 1, 4, 5, 8, 11, or 20; or a pharmaceutically acceptable salt thereof, to the animal in need thereof. In another aspect, is a method of treating an animal with MMVD, CHF and/or asymptomatic heart failure, by administering a therapeutic amount of a Formula (1A) compound with a 5c-5HT2B $IC_{50}$<10 nM that is any one of Example 1, 4, 5 or 8; or a pharmaceutically acceptable salt thereof, to the animal in need thereof. In another aspect, is a method of treating an animal with MMVD, CHF and/or asymptomatic heart failure, by administering a therapeutic amount of a Formula (1A) compound with a 5c-5HT2B $IC_{50}$<1 nM that is any one of Example 1, 4 or 5; or a pharmaceutically acceptable salt thereof, to the animal in need thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1B) compound; or a pharmaceutically acceptable salt thereof. In another aspect, is a method of treating an animal with MMVD, CHF and/or asymptomatic heart failure, by administering a therapeutic amount of a Formula (1B) compound with a 5c-5HT2B $IC_{50}$<1000 nM that is any one of Example 6-7, 12-13 or 25-28; or a pharmaceutically acceptable salt thereof. In another aspect, is a method of treating an animal with MMVD, CHF and/or asymptomatic heart failure, by administering a therapeutic amount of a Formula (1B) compound with a 5c-5HT2B $IC_{50}$<100 nM that is any one of Example 6-7, 12 or 25-26; or a pharmaceutically acceptable salt thereof. In another aspect, is a method of treating an animal with MMVD, CHF and/or asymptomatic heart failure, by administering a therapeutic amount of a Formula (1B) compound with a 5c-5HT2B $IC_{50}$<10 nM that is any one of Example 6-7 or 25; or a pharmaceutically acceptable salt thereof. In another aspect, is a method of treating an animal with MMVD, CHF and/or asymptomatic heart failure, by administering a therapeutic amount of a Formula (1B) compound with a 5c-5HT2B $IC_{50}$<1 nM that is Example 6; or a pharmaceutically acceptable salt thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1C) compound; or a pharmaceutically acceptable salt thereof, to the animal in need thereof.

In another aspect, is a method of treating an animal with MMVD, CHF and/or asymptomatic heart failure, by administering a therapeutic amount of a Formula (1C) compound with a 5c-5HT2B $IC_{50}$<1000 nM that that is one of Example 18, 22 or 23, or a pharmaceutically acceptable salt thereof, to the animal in need thereof. In another aspect, is a method of treating an animal with MMVD, CHF and/or asymptomatic heart failure, by administering a therapeutic amount of a Formula (1C) compound with a 5c-5HT2B $IC_{50}$<100 nM that that is Example 22 or 23, or a pharmaceutically acceptable salt thereof, to the animal in need thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1D) compound; or a pharmaceutically acceptable salt thereof, to the animal in need thereof. In another aspect, is a method of treating an animal with MMVD, CHF and/or asymptomatic heart failure, by administering a therapeutic amount of a Formula (1D) compound; or a pharmaceutically acceptable salt thereof, to the animal in need thereof. In another aspect, is a method of treating an animal with MMVD, CHF and/or asymptomatic heart failure, by administering a therapeutic amount of a Formula (1D) compound with a 5c-5HT2B $IC_{50}$<10 nM that is Example 2 or 3; or a pharmaceutically acceptable salt thereof, to the animal in need thereof. In another aspect, is a method of treating an animal with MMVD, CHF and/or asymptomatic heart failure, by administering a therapeutic amount of a Formula (1D) compound with a 5c-5HT2B $IC_{50}$<1 nM that is Example 2; or a pharmaceutically acceptable salt thereof, to the animal in need thereof. In another aspect, the animal is a companion animal. In another aspect, the companion animal is canine.

In another aspect, is a method of treating an animal with MMVD, CHF and/or asymptomatic heart failure, by administering a therapeutic amount of a Formula (1E) compound; or a pharmaceutically acceptable salt thereof, to the animal in need thereof. In another aspect, is a method of treating an animal with MMVD, CHF and/or asymptomatic heart failure, by administering a therapeutic amount of a Formula (1E) compound with a 5c-5HT2B $IC_{50}$<1 nM that is Example 24, or a pharmaceutically acceptable salt thereof, to the animal in need thereof. In another aspect, the animal is a companion animal. In another aspect, the companion animal is canine.

In yet another aspect of the invention, is the use of a Formula (1) compound, or a pharmaceutically acceptable salt thereof, to prepare a medicament for treating an animal with MMVD, CHF and/or asymptomatic heart failure. In the uses described below, the Example #'s are interchangeable with each respective compound name as described herein. In another aspect, is the use of a Formula (1) compound, with a 5c-5HT2B $IC_{50}$<1000 nM, wherein said compound is any one of Example 1-13, 18-20 or 22-28; or a pharmaceutically acceptable salt thereof, to prepare a medicament for treating an animal with MMVD, CHF and/or asymptomatic heart failure. In another aspect, is the use of a Formula (1) compound, with a 5c-5HT2B $IC_{50}$<500 nM, wherein said compound is any one of Example 1-12, 19-20 or 22-28; or a pharmaceutically acceptable salt thereof, to prepare a medicament for treating an animal with MMVD, CHF and/or asymptomatic heart failure. In another aspect, is the use of a Formula (1) compound, with a 5c-5HT2B $IC_{50}$<100 nM, wherein said compound is any one of Example 1-8, 11-12, 20 or 22-26; or a pharmaceutically acceptable salt thereof, to prepare a medicament for treating an animal with MMVD, CHF and/or asymptomatic heart failure. In another aspect, is the use of a Formula (1) compound, with a 5c-5HT2B $IC_{50}$<10 nM, wherein said compound is any one of Example 1-8, 24 or 25; or a pharmaceutically acceptable salt thereof, to prepare a medicament for treating an animal with MMVD, CHF and/or asymptomatic heart failure. In another aspect, is the use of a Formula (1) compound, with a 5c-5HT2B $IC_{50}$<1 nM, wherein said compound is any one of Example 1, 2, 4-6 or 24; or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1A), Formula (1B), Formula (1C), Formula (1D) or Formula (1E) compound, or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1A) compound; or a pharmaceutically acceptable salt thereof, to prepare a medicament for treating an animal with MMVD, CHF and/or asymptomatic heart failure. In another aspect, is the use of a Formula (1A) compound with a 5c-5HT2B $IC_{50}$<500 nM that is any one of Example 1, 4, 5, 8, 11, 19 or 20; or a pharmaceutically acceptable salt thereof, to prepare a medicament for treating an animal with MMVD, CHF and/or asymptomatic heart failure. In another aspect, is the use of a Formula (1A) compound with a 5c-5HT2B $IC_{50}$<100 nM that is any one of Example 1, 4, 5, 8, 11 or 20; or a pharmaceutically acceptable salt thereof, to prepare a medicament for treating an animal with MMVD, CHF and/or asymptomatic heart failure. In another aspect, is the use of a Formula (1A) compound with a 5c-5HT2B $IC_{50}$<10 nM that is any one of Example 1, 4, 5 or 8; or a pharmaceutically acceptable salt thereof, to prepare a medicament for treating an animal with MMVD, CHF and/or asymptomatic heart failure. In another aspect, is the use of a Formula (1A) compound with a 5c-5HT2B $IC_{50}$<1 nM that is any one of Example 1, 4 or 5; or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1B) compound, or a pharmaceutically acceptable salt thereof, to prepare a medicament for treating an animal with MMVD, CHF and/or asymptomatic heart failure. In another aspect, is the use of a Formula (1B) compound with a 5c-5HT2B $IC_{50}$<1000 nM that is any one of Example 6, 7 12-13 or 25-28, or a pharmaceutically acceptable salt thereof, to prepare a medicament for treating an animal with MMVD, CHF and/or asymptomatic heart failure. In another aspect, is the use of a Formula (1B) compound with a 5c-5HT2B $IC_{50}$<500 nM that is any one of Example 6-7, 12 or 25-28, or a pharmaceutically acceptable salt thereof, to prepare a medicament for treating an animal with MMVD, CHF and/or asymptomatic heart failure.

In another aspect, is the use of a Formula (1B) compound with a 5c-5HT2B $IC_{50}$<100 nM that is any one of Example 6-7, 12, 25 or 26, or a pharmaceutically acceptable salt thereof, to prepare a medicament for treating an animal with MMVD, CHF and/or asymptomatic heart failure. In another aspect, is the use of a Formula (1B) compound with a 5c-5HT2B $IC_{50}$<10 nM that is any one of Example 6, 7 or 25, or a pharmaceutically acceptable salt thereof, to prepare a medicament for treating an animal with MMVD, CHF and/or asymptomatic heart failure. In another aspect, is the use of a Formula (1B) compound with a 5c-5HT2B $IC_{50}$<1 nM that is Example 6; or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1C) compound; or a pharmaceutically acceptable salt thereof, to prepare a medicament for treating an animal with MMVD, CHF and/or asymptomatic heart failure. In another aspect, is the use of a Formula (1C) compound with a 5c-5HT2B $IC_{50}$<1000 nM that is any one of Example 18, 22 or 23, or a or a pharmaceutically acceptable salt thereof, to prepare a medicament for treating an animal with MMVD, CHF and/or asymptomatic heart failure. In another aspect, is the use of a Formula (1C) compound with a 5c-5HT2B $IC_{50}$<100 nM that that is Example 22 or 23, or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1D) compound; or a pharmaceutically acceptable salt thereof, to prepare a medicament for treating an animal with MMVD, CHF and/or asymptomatic heart failure. In another aspect, is the use of a Formula (1D) compound with a 5c-5HT2B $IC_{50}$<10 nM that is Example 2 or 3; or a pharmaceutically acceptable salt thereof, to prepare a medicament for treating an animal with MMVD, CHF and/or asymptomatic heart failure. In another aspect, is the use of a Formula (1D) compound with a 5c-5HT2B $IC_{50}$<1 nM that is Example 2, or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect, is the use of a Formula (1E) compound, or a pharmaceutically acceptable salt thereof, to prepare a medicament for treating an animal with MMVD, CHF and/or asymptomatic heart failure. In another aspect, is the use of a Formula (1E) compound with a 5c-5HT2B $IC_{50}$<1 nM that is Example 24; or a pharmaceutically acceptable salt thereof, to prepare a medicament for treating an animal with MMVD, CHF and/or asymptomatic heart failure. In another aspect, the animal is a companion animal. In another aspect, the companion animal is canine.

In another aspect of the invention, is a method of treating an animal with MMVD, CHF and/or asymptomatic heart failure, by administering a therapeutically effective amount of a Formula (1) compound of the invention; or a pharmaceutically acceptable salt thereof, to the animal in need thereof in combination with at least one additional cardiovascular agent. In another aspect of the invention, is a method of treating an animal with MMVD, CHF and/or asymptomatic heart failure, by administering a therapeutically effective amount of a Formula (1A) compound; a Formula (1A) compound with a 5c-5HT2B $IC_{50}$<500 nM that is any one of Example 1, 4, 5, 8, 11, 19 or 20; a Formula (1A) compound with a 5c-5HT2B $IC_{50}$<100 nM that is any one of Example 1, 4, 5, 8, 11 or 20; a Formula (1A) compound with a 5c-5HT2B $IC_{50}$<10 nM that is any one of Example 1, 4, 5 or 8; a Formula (1A) compound with a 5c-5HT2B $IC_{50}$<1 nM that is any one of Example 1, 4 or 5, or a pharmaceutically acceptable salt thereof, to the animal in need thereof in combination with at least one additional cardiovascular agent. In another aspect of the invention, is a method of treating an animal with MMVD, CHF and/or asymptomatic heart failure, by administering a therapeutically effective amount of a Formula (1B) compound; a Formula (1B) compound with a 5c-5HT2B $IC_{50}$<1000 nM that is any one of Example 6, 7, 12, 13 or 25-28; a Formula (1B) compound with a 5c-5HT2B $IC_{50}$<500 nM that is any one of Example 6, 7, 12 or 25-28; a Formula (1B) compound with a 5c-5HT2B $IC_{50}$<100 nM that is any one of Example 6, 7, 12 or 25-26; a Formula (1B) compound with a 5c-5HT2B $IC_{50}$<10 nM that is any one of Example 6, 7 or 25; a Formula (1B) compound with a 5c-5HT2B $IC_{50}$<1 nM that is Example 6; or a pharmaceutically acceptable salt thereof, to the animal in need thereof in combination with at least one additional cardiovascular agent. In another aspect of the invention, is a method of treating an animal with MMVD, CHF and/or asymptomatic heart failure, by administering a therapeutically effective amount of a Formula (1C) compound; a Formula (1C) compound with a 5c-5HT2B $IC_{50}$<1000 nM that is any one of Example 18, 22 or 23; a Formula (1C) compound with a 5c-5HT2B $IC_{50}$<100 nM that is Example 22 or 23; or a pharmaceutically acceptable salt thereof, to the animal in need thereof in combination with at least one additional cardiovascular agent. In another aspect of the invention, is a method of treating an animal with MMVD, CHF and/or asymptomatic heart failure, by administering a therapeutically effective amount of a Formula (1D) compound; a Formula (1D) compound with a 5c-5HT2B $IC_{50}$<10 nM that is Example 2 or 3; a Formula (1 D) compound with a 5c-5HT2B $IC_{50}$<1 nM that is Example 2; or a pharmaceutically acceptable salt thereof, to the animal in need thereof in combination with at least one additional cardiovascular agent. In another aspect of the invention, is a method of treating an animal with MMVD, CHF and/or asymptomatic heart failure, by administering a therapeutically effective amount of a Formula (1E) compound; a Formula (1E) compound with a 5c-5HT2B $IC_{50}$<1 nM that is Example 24, or a pharmaceutically acceptable salt thereof, to the animal in need thereof in combination with at least one additional cardiovascular agent. In another aspect, the animal is a companion animal.

In another aspect, the animal is canine. In another aspect, the at least one additional cardiovascular agent is selected from the group consisting of: an ACE inhibitor and/or a diuretic. In another aspect, non-limiting examples of an ACE inhibitor include: enalapril, captopril, benazepril, ramipril, and the like. In another aspect, non-limiting examples of a diuretic include: furosemide, chlorothiazide, hydrochlorothiazide, spironolactone, amiloride, triamterene, isosorbide, and the like.

DESCRIPTION OF THE INVENTION

Definitions

For purposes of the invention, as described and claimed herein, the following terms and phrases are defined as follows:

"About", when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Additional veterinary (or pharmaceutical) agent(s)" as used herein, unless otherwise indicated, refers to other veterinary or pharmaceutical compounds or products (i.e., drugs) that provide a therapeutically effective amount of said agent(s) that are useful for the treatment of MMVD, CHF, and/or asymptomatic heart failure in an animal, preferably canine.

"Alkyl", as used herein, unless otherwise indicated, refers to saturated monovalent hydrocarbon alkane radicals of the general formula $C_nH_{2n+1}$. The alkane radical can be straight or branched and can be unsubstituted or substituted. For example, the term "$(C_1-C_4)$alkyl" refers to a monovalent, straight or branched aliphatic group containing 1 to 4 carbon atoms; similarly, $C_1-C_3$ alkyl refers to a monovalent, straight or branched aliphatic group containing 1 to 3 carbon atoms, etc. Non-exclusive examples of $(C_1-C_4)$ alkyl groups include, but are not limited to methyl, ethyl, propyl, isopropyl, sec-butyl, t-butyl, n-propyl, n-butyl, i-butyl, s-butyl, and the like. The alkyl moiety can be attached to the chemical moiety by any one of the carbon atoms of the aliphatic chain.

"Animal(s)", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals. Non-exclusive examples of a companion animal include: dog, cat, and horse. The preferred companion animal is canine.

"Asymptomatic (occult, preclinical) heart failure" as used herein, unless otherwise indicated, refers to any contractile disorder or disease of the heart which is due to MMVD.

"Carbocycle", as used herein, unless otherwise indicated, includes fully saturated carbocyclic alkyl moieties, i.e., a 5- to 6-membered ring containing only carbon atoms; i.e., cyclopentyl and cyclohexyl. The carbocycle group can be optionally substituted as described herein.

"Compound(s) of the invention", unless otherwise indicated, refers to the c5-HT2B antagonists as described for Formula (1), Formula (1A), Formula (1B), Formula (1C), Formula (1D) and Formula (1E) compounds; and in particular, Example 1 through Example 28 compounds; and/or pharmaceutically acceptable salts thereof.

"Congestive heart failure", or "heart failure" unless otherwise indicated, refers to a manifested process wherein the heart is unable to keep up with the demands of blood supply to the body and generally results in fluid buildup in the lungs resulting from increased cardiac and pulmonary pressures. The term(s) also relate to any contractile disorder or disease of the heart. Clinical manifestations are as a rule the result of changes to the heart's cellular and molecular components and to mediators that drive homeostatic control that leads to an increase in heart size and deterioration of cardiac function.

"Halogen" or "halo", as used herein, unless otherwise indicated, refers to fluoro, chloro, bromo and iodo. Preferred halo include fluoro and chloro.

"Heteroaryl" as used herein, unless otherwise indicated, refers to a 5- to 6-membered aromatic monocyclic ring or an 10- to 11-membered fused aromatic ring where said monocyclic- and fused-ring moiety contains one or more heteroatoms each independently selected from N, O and S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, quinolinyl, isoquinolinyl, benzimidazolyl, indazolyl, benzotriazolyl, thieno[2,3-c]pyridine, thieno[3,2-b]pyridine, benzo[1,2,5]thiadiazole, and the like. Preferred heteroaryls include: thiazolyl, isothiazolyl, thiophenyl, pyridinyl and indolyl. The heteroaryl group can be attached to the chemical moiety by any one of the carbon atoms or nitrogen heteroatoms within the monocyclic or fused ring.

"Myxomatous mitral valve degeneration (MMVD)", unless otherwise indicated, refers to the manifested process of mitral valve degeneration. MMVD is generally detected as a heart murmur by auscultation. MMVD also includes synonymous medicinal terms: mitral valve disease (MVD); degenerative mitral valve disease (DMVD); chronic valve disease (CVD); chronic valvular heart disease (CVHD); and atrial ventricular valvular insufficiency (AVVI).

"Optionally substituted" as used herein unless otherwise indicated, means that the referenced group can be substituted with one or more additional group(s) individually and independently selected from the listed group which depends on valency of the referenced group.

"Pharmaceutically acceptable" as used herein, unless otherwise indicated, indicates that the substance or composition must be compatible chemically and/or toxicologically, with the other ingredients comprising a formulation, composition, and/or the animal being treated therewith. The use of the phrase "and pharmaceutically acceptable salt(s)" can be interchanged with "or a pharmaceutically acceptable salt(s)".

"Therapeutically effective amount", unless otherwise indicated, refers to an amount of the compound of the invention that (i) treat MMVD, CHF, and/or asymptomatic heart failure in an animal (ii) attenuates, ameliorates, or eliminates one or more symptoms of MMVD, CHF, and/or asymptomatic heart failure in an animal, or (iii) prevents or delays the onset of MMVD, CHF, and/or asymptomatic heart failure in an animal.

"Treatment", "treating", "treat", and the like, as used herein, unless otherwise indicated, refers to alleviating, halting, or slowing the progression of MMVD, CHF, and/or asymptomatic heart failure in an animal. As used herein, these terms also encompass, depending on the condition of the animal, preventing the onset of a disorder or condition, or of symptoms associated with a disorder or condition, including reducing the severity of a disorder or condition or symptoms associated therewith. Thus, treatment can refer to administration of a compound of the invention to an animal that is not at the time of administration diagnosed with CHF.

Myxomatous mitral valve degeneration (MMVD) is the most common acquired type of heart disease and new heart murmurs in older dogs. A heart murmur is a sound heard with every heartbeat and is caused by turbulent blood flow in the heart. MMVD is a manifestation of a process that can affect the mitral valve. MMVD affects primarily small breed dogs later in life but can affect larger breed dogs. Some smaller breed dogs are affected earlier in life than others with the Cavalier King Charles Spaniel being the most prominent breed described to date.

The mitral valve is the valve between the left atrium and the left ventricle. Oxygenated blood from the lungs enters the left atrium, passes through the mitral valve into the left ventricle and subsequently pumped to the body. The mitral valve closes when the left ventricle contracts which prevents blood from flowing back into the left atrium. A healthy mitral valve is thin and supple and is anchored in place by chordae tendonae (CT). Myxomatous degeneration is a process that occurs when the valve becomes thickened with formation of small nodules which prevent complete closing of the valves allowing back flow (mitral regurgitation) of blood into the left atrium. Over time, the atrium and ventricles compensate by enlarging and the leak progressively worsens. As leaking volume increases, atrial pressure increases. In some instances, CT may rupture causing a partially unanchored mitral valve (mitral valve pro-lapse). The increase in pressure is transmitted to the lungs leading to CHF.

A heart murmur is generally the earliest means by which MMVD can be detected. After the murmur is detected, MMVD symptoms may not appear for three to four years. Often the first outward sign of worsening MMVD is a cough or increased respiratory effort which can be due to airway pressure from the enlarged heart and/or fluid congestion in the lungs and heart.

There are no medications that are proven to prevent the progression of MMVD, particularly in the early stages of the disease. Treatments are administered to manage MMVD, CHF and/or asymptomatic heart failure, including: furosemide, pimobendan, an ACE inhibitor (e.g., enalapril) and spironolactone, either alone or in combination. Furosemide is a potent diuretic and removes water from the body thereby decreasing pulmonary fluid congestion. Pimobendan helps the heart work more effectively, aids in decreasing cardiac remodeling and has been shown to improve survival in MMVD patients. ACE inhibitors and spironolactone block deleterious compensatory mechanisms that occur with severe heart disease and have been shown to prolong survival as well. Side effects of these drugs include allergic reaction, staggering, loss of appetite, lethargy, diarrhea, and fainting. Other medications that are sometimes used in treatment of CHF include hydrochlorothiazide, amlodipine, torsemide, and digoxin.

Despite development of new drugs and treatment regimens, uncertainty remains about when to treat and what the best interventions are for some of these animals. In 2009, an objective classification system was developed to categorize heart disease that is based on risk factors and clinical and diagnostic imaging signs.

Heart failure is divided in different stages, which were defined by different classification systems, e.g. the International Small Animal Cardiac Health Council (ISACHC), the New York Heart Association (NYHA) functional classification systems and the currently used classification according to the Consensus Statements of the American College of Veterinary Internal Medicine (ACVIM), 2009. To remove any ambiguity between classification systems, the classification systems described below are to be considered synonymous.

Classification according to the International Small Animal Cardiac Health Council (ISACHC) System: Class I: asymptomatic (also known as occult or preclinical); Class IA: no evidence of compensation for underlying heart disease (no volume overload or pressure overload detected radiographically or echocardiographically); Class IB: clinical signs of compensation for underlying heart disease (volume overload or pressure overload detected radiographically or echocardiographically); Class II: mild to moderate heart failure with clinical signs at rest or with mild exercise (treatment required); Class III: advanced heart failure; clinical signs of severe congestive heart failure; Class IIIA: home treatment possible; and Class IIIB: requires hospitalization.

New York Heart Association (NYHA) functional classification system: Class I: describes patients with asymptomatic heart disease (e.g., chronic valvular heart disease (CVHD) is present, but no clinical signs are evident even with exercise); Class II: describes patients with heart disease that causes clinical signs only during strenuous exercise; Class III: describes patients with heart disease that causes clinical signs with routine daily activities or mild exercise; and Class IV: describes patients with heart disease that causes severe clinical signs even at rest.

The ACVIM system describes four basic stages of heart disease and failure: Stage A: patients at high risk for developing heart disease but that currently have no identifiable structural disorder of the heart; Stage B: patients with structural heart disease (e.g., the typical murmur of mitral valve regurgitation is present), but that have never developed clinical signs caused by heart failure (because of important clinical implications for prognosis and treatment, the panel further subdivided Stage B into Stage B1 and B2). Stage B1: asymptomatic patients that have no radiographic or echocardiographic evidence of cardiac remodeling in response to CVHD. Stage B2: asymptomatic patients that have hemodynamically significant valve regurgitation, as evidenced by radiographic or echocardiographic findings of left sided heart enlargement. Stage C: patients with past or current clinical signs of heart failure associated with structural heart disease. Stage D: patients with end-stage disease with clinical signs of heart failure caused by CVHD that are refractory to standard therapy.

The pathology of the heart begins with ISACHC Class I, NYHA Class I and ACVIM stage B2 in which cardiac murmur or cardiac chamber enlargement, but no clinical symptoms are present (ISACHC Class I or asymptomatic/occult/preclinical stage). Clinical symptoms become manifest in the course of progression of the disease (ISACHC Class II or III, NYHA class II, III or IV, ACVIM stage C and D). Since the compounds of the invention have an affinity to c5-HT2B, the compounds may provide a potentially new drug to veterinarians for treating MMVD, CHF and/or asymptomatic heart failure.

The Formula (1) compounds of the invention can be synthesized by synthetic routes that include processes analogous to those well known in the chemical arts, particularly in light of the description contained herein. The starting materials are generally available from commercial sources such as Aldrich Chemicals (Milwaukee, WI), Combi-Blocks (San Diego, CA), Synthonix Chemicals (Wake Forest, NC), Enamine (Monmouth Jct. NJ) and others; or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compound of the invention, and key intermediates. A more detailed description of the individual reaction steps can be found in the Examples section. The skilled person will appreciate that the compound of the invention could be made by methods other than those herein described by adaptation of the methods herein described and/or adaptation of methods known in the art, for example the art described herein, or using standard textbooks such as "Comprehensive Organic Transformations—A Guide to Functional Group Transformations", RC Larock, Wiley-VCH (1999 or later editions).

Schemes 1 outlines the general procedure for the preparation and isolation of the compound of the invention. It is to be understood, however, that the invention, as fully described herein and as recited in the claims, is not intended to be limited by the details of the following scheme or modes of preparation.

In the Examples and methods described below, the following reactants and miscellaneous abbreviations include: room temperature (RT); tetrahydrofuran (THF); dichloromethane (DCM); N, N-dimethylformamide (DMF); methanol (MeOH); N,N-diisopropylethylamine (DIPEA); (1-[Bis(dimethylamino)methylene]-1H-1,2,3-triazolo[4,5-b]pyridinium 3-oxide hexafluorophosphate (HATU); N-methylmorpholine (NMM); N,N-diisopropylethylamine (i-Pr$_2$NEt); sodium triacetoxyborohydride (NaBH(OAc)$_3$; acetic acid (AcOH); tert-butyloxycarbonyl (BOC); trifluoroacetic acid (TFA); lithium hydroxide (LiOH); caesium carbonate (Cs$_2$CO$_3$); copper(I) iodide (CuI); 1,2-dichloroethane (DCE); water (H$_2$O); Hank's Balanced Salt Solution (HBSS); fetal bovine serum (FBS); Dulbecco's modified eagle medium (DMEM); Minimal essential media (MEM); and (4-(2-hydroxyethyl)-1-piperazineethanesulfonic acid (HEPES).

The pharmaceutically acceptable salts of compound of the instant invention may also be prepared in a conventional manner. For example, a solution of a free base can be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

A Formula (1) compound of the invention can be used in its native form or as a salt. In cases where forming a stable nontoxic acid or base salt is desired, administration of the compound as a pharmaceutically acceptable salt can be appropriate. Pharmaceutically acceptable salts of the compound of the instant invention include, but are not limited to: acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, and trifluoroacetate salts.

The Formula (1) compounds of the invention can be prepared as described by the Scheme and procedures described herein.

Scheme 1. Preparation of Formula (1) Compounds

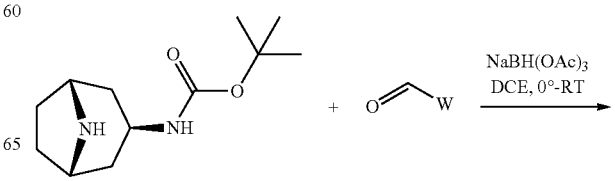

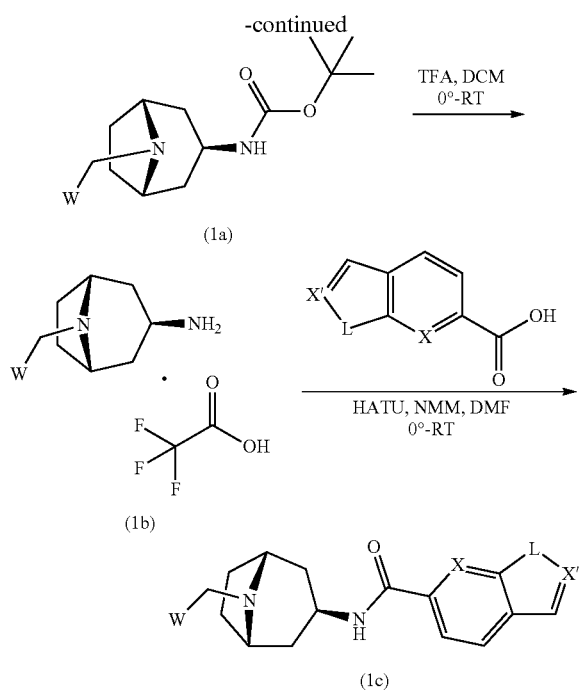

(1a)

(1b)

(1c)

wherein W is Ring A (optionally substituted ((R⁴)ₙ) wherein R⁴ and n are as described herein), X, L and X' are also as described herein. The first Boc-protected amine intermediate (1a) can be prepared by standard reductive alkylation technology, the reducing agent (sodium triacetoxyborohydride) can be replaced with other reducing agents such as sodium cyanoborohydride, sodium borohydride or Pd/C (with $H_2$ or $Et_3SiH$). After deprotecting the Boc-amine with TFA, the amine (1 b) can then be coupled with pyrrolo-pyridine acid (or indole-, indazole- or benzofuran-carboxylic acids) using classic amide coupling agents such as HATU.

The Formula (1) compounds of the invention are useful as a 5-HT2B antagonist for the treatment of MMVP, CHF and/or asymptomatic heart failure in animals, particularly canines (c5-HT2B). Another aspect of the invention is a veterinary composition comprising a therapeutically effective amount of a Formula (1) compound of the invention, or a pharmaceutically acceptable salt thereof. Another aspect of the invention is a veterinary composition comprising a therapeutically effective amount of a Formula (1) compound of the invention, or a pharmaceutically acceptable salt thereof, and a pharmaceutically acceptable excipient. Formula (1) compounds of the invention (including the compositions and processes used therein), or a pharmaceutically acceptable salt thereof, can be used in the manufacture of a medicament for the therapeutic applications described herein.

A Formula (1) compound of the invention, or a pharmaceutically acceptable salt thereof, can be administered alone or in a formulation appropriate to the specific use envisaged and the species of animal being treated. Generally, it will be administered as a formulation in association with one or more pharmaceutically acceptable excipients. The term "excipient", is used herein to describe any ingredient other than the Formula (1) compound of the invention or any additional veterinary agent. The choice of excipient(s) will to a large extent depend on factors such as the particular mode of administration, the effect of the excipient(s) on solubility and stability, and the nature of the dosage form. In addition to the excipient(s), the amount of the compound of the invention that is administered and the dosage regimen for treating a condition or disorder with the compound depends on a variety of factors, including the age, weight, sex and medical condition of the animal, the severity of the disease, the route and frequency of administration, and thus may vary widely.

In one aspect, the veterinary composition comprises a Formula (1) compound of the invention, or a pharmaceutically acceptable salt thereof, with a pharmaceutically acceptable excipient. The concentration range will vary depending on the composition (e.g., oral or injectable). For an oral dose, the range of active (i.e., compound of the invention) is about 0.1 to about 10 mg/kg, preferably from about 0.5 to about 5 mg/kg, and even more preferably from about 0.5 to about 3 mg/kg, and most preferably from about 0.5 to about 1.5 mg/kg. For an injectable solution, the range of active is about 0.1 to about 50 mg/mL, and preferably from about 0.5 to about 25 mg/mL, and more preferably from about 1 to about 10 mg/mL, and even more preferably from about 2 to about 5 mg/mL. The preferable route of administration is oral. The concentration ranges and preferred concentration ranges are considered to be therapeutically effective doses. Further, dose range and preferred dose range can be higher or lower than the concentrations described herein.

The formulations can be prepared using conventional dissolution and mixing procedures. Such compositions and methods for their preparation can be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a Formula (1) compound of the invention, or a pharmaceutically acceptable salt thereof, with at least one pharmaceutically acceptable excipient. Suitable excipients are well known to those skilled in the art and include materials such as carbohydrates, waxes, water soluble and/or swellable polymers, hydrophilic or hydrophobic materials, gelatin, oils, solvents, water, and the like. The particular excipient(s) will depend upon the means and purpose for which the compound of the invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the invention or veterinary composition thereof) or aid in the manufacturing of the veterinary product (i.e., medicament). A Formula (1) compound of the invention will typically be formulated into veterinary dosage forms to provide an easily controllable dosage form for administration.

The methods by which the Formula (1) compound of the invention can be administered include oral and injectable (e.g., parenteral, subcutaneous and intramuscular).

The Formula (1) compound of the invention, or a pharmaceutically acceptable salt thereof, can be administered orally by capsule, bolus, tablet, powders, lozenges, chews, multi and nano-particulates, gels, solid solution, films, sprays, or liquid form. This is a preferred method of administration and as such it is desirable to develop the compound for oral administration. Such formulations can be employed as fillers in soft or hard capsules, soft or hard palatable chews, which typically comprise an excipient, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet.

Injectable formulations can be prepared in the form of a sterile solution, which may contain other substances, for example enough salts or glucose to make the solution isotonic with blood. Acceptable liquid excipients include vegetable oils such as sesame oil and cotton seed oil, glycerides such as triacetin, esters such as benzyl benzoate, isopropyl myristate and fatty acid derivatives of propylene glycol, as well as organic solvents such as pyrrolidin-2-one, benzyl alcohol and glycerol formal. The formulations are prepared by dissolving or suspending compound of the invention alone or with an additional veterinary agent in the liquid excipient(s) such that the final formulation contains from about 0.01 to 30% by weight of the active ingredient.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they can be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of a compound of the invention used in the preparation of an injectable solution can be increased by using solubility-enhancing agents.

Administration of a Formula (1) compound of the invention, or a pharmaceutically acceptable salt thereof, is contemplated to be once or twice daily. Preferably, once a day (qd).

The composition of the invention can be administered alone, as described above, or in combination with at least one other additional veterinary agent thereby providing a broader spectrum of veterinary utility. These at least one other additional veterinary agents, including pharmaceutical agents, can be dosed simultaneously with the compound of the invention, or anytime through-out the duration of treatment of the animal.

The following list of additional pharmaceutical (veterinary) cardiovascular agents together with which the compound of the invention can be used to treat cardiac disease (e.g., MMVD, CHF, and/or asymptomatic heart failure) is intended to illustrate the possible combinations, but not to impose any limitation thereof. Non-limiting examples of additional pharmaceutical (veterinary) agents include: diuretics (e.g., furosemide, chlorothiazide, indapamide, triamterene, hydrochlorothiazide, and the like) to reduce edema and effusion; aldosterone antagonists (e.g., spironolactone, eplerenone, and the like) to reduce aldosterone-mediated myocardial fibrosis, possibly slowing or halting the progression of heart disease and block the reabsorption of sodium which encourages water loss; and an ACE inhibitor (e.g. enalapril, accupril, captopril, ramipril, and the like) to inhibit the action of angiotensin-converting enzyme, producing a balanced vasodilation by relaxing blood vessels.

The veterinary composition for application to an animal can be packaged in a variety of ways depending upon the method used for administering the compound of the invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

A Formula (1) compound of the invention (including the compositions and processes used therein), or a pharmaceutically acceptable salt thereof, may also be used in the manufacture of a medicament for the therapeutic applications described herein.

The Formula (1) compound structures in the examples below were confirmed by one or more of the following methods: proton magnetic resonance spectroscopy, and mass spectroscopy. Proton magnetic resonance (1H NMR) spectra were determined using a Bruker spectrometer operating at a field strength of 400 megahertz (MHz). Chemical shifts are reported in parts per million (PPM, δ) downfield from an internal tetramethylsilane standard or residual protonated NMR solvents. Mass spectra (MS) data were obtained using Agilent mass spectrometer (1290 Infinity II) with multimode electrospray and atmospheric pressure chemical ionization (MM-ES+APCI) method. High-performance liquid chromatography (HPLC) performed on Agilent 1260 infinity II with X-Bridge C8 (50×4.6) mm, 3.5 μm column. The mobile phase was a binary gradient of acetonitrile and 10 mM ammonium bicarbonate in water with a flow rate of 1.0 mL/minute.

EXAMPLES

The following examples provides a more detailed description of the process conditions for preparing the Formula (1) compounds of the invention. It is to be understood, however, that the invention, as fully described herein and as recited in the claims, is not intended to be limited by the details of the following modes of preparation.

Intermediates

Synthesis of (1R,3s,5S)-8-(4-chlorobenzyl)-8-azabicyclo[3.2.1]octan-3-amine.2,2,2-trifluoroacetate

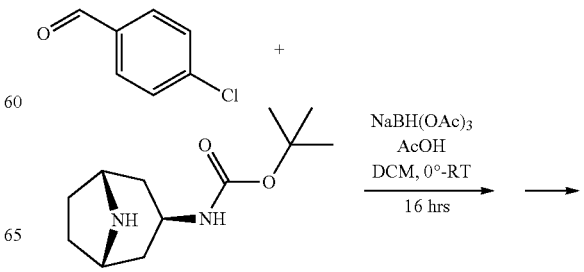

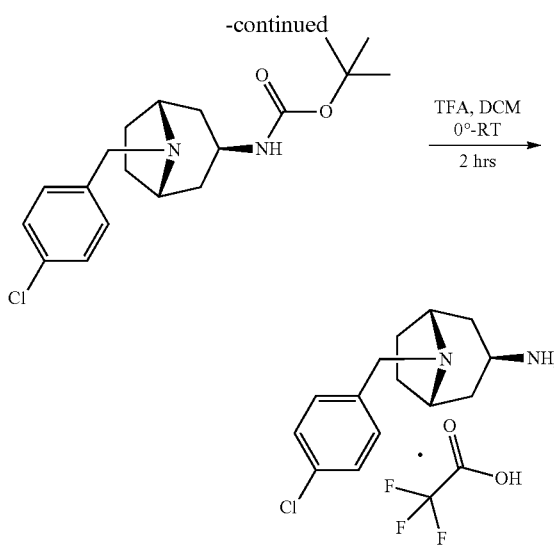

26); l) thiazole-2-carbaldehyde (Example 27); and m) 4-methylthiazole-2-carbaldehyde (Example 28).

Synthesis of (1R,3s,5S)-8-phenyl-8-azabicyclo[3.2.1]octan-3-amine.2,2,2-trifluoroacetate

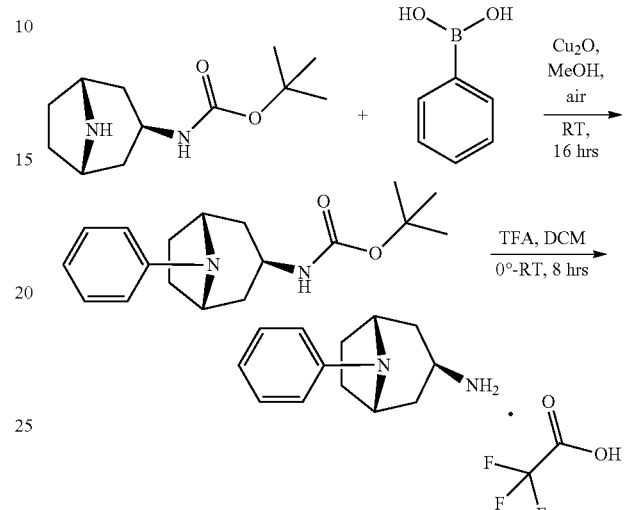

This N-phenyl intermediate was prepared by a Chan-Lam reaction using phenyl boronic acid as the source of phenyl and catalyzed with copper oxide, copper acetate is a common alternative to this catalyst. The intermediate was then deprotected with TFA to give the intermediate used in the synthesis of Example 17.

Step-1: Synthesis of tert-butyl ((1R,3s,5S)-8-phenyl-8-azabicyclo[3.2.1]octan-3-yl)carbamate. To a stirred solution of phenyl boronic acid (300 mg, 2.46 mmol) in methanol (5.0 mL) were added tert-butyl ((1R,3s,5S)-8-azabicyclo[3.2.1]octan-3-yl)carbamate (668.21 mg, 2.95 mmol), and $Cu_2O$ (17.85 mg, 0.12 mmol). Resulting reaction mixture was stirred at room temperature for 16 hours under air atmosphere. After completion, reaction mixture was diluted with water and extracted with ethyl acetate. Combined organic layer was washed with brine, dried over sodium sulphate, filtered and evaporated under reduced pressure. Crude product was purified by combiflash column chromatography (30% ethyl acetate-hexane) to afford tert-butyl ((1R,3s,5S)-8-phenyl-8-azabicyclo[3.2.1]octan-3-yl)carbamate (100.0 mg) as an off white solid.

Step-2: Synthesis of (1R,3s,5S)-8-phenyl-8-azabicyclo[3.2.1]octan-3-amine. To a stirred solution of tert-butyl ((1R,3s,5S)-8-phenyl-8-azabicyclo[3.2.1]octan-3-yl)carbamate (100.0 mg, 0.33 mmol) in DCM (5.0 mL) was added TFA (0.13 mL, 1.66 mmol) at 0° C. Resulting reaction mixture was stirred at room temperature for 2 hours. After completion, reaction mixture was concentrated under reduced pressure and dried to afford (1R,3s,5S)-8-phenyl-8-azabicyclo[3.2.1]octan-3-amine.2,2,2-trifluoroacetate (50 mg) as white solid. 1H NMR (400 MHz, DMSO-d6) δ 1.62-1.68 (m, 4H), 1.75-1.77 (m, 2H), 1.97-1.99 (m, 2H), 3.56-3.58 (m, 1H), 4.33 (bs, 2H), 6.65 (t, J=7.20 Hz, 1H), 6.82 (d, J=8.04 Hz, 2H), 7.20 (t, J=7.84 Hz, 2H), 7.63 (bs, 2H).

Step-1: Synthesis of tert-butyl ((1R,3s,5S)-8-(4-chlorobenzyl)-8-azabicyclo[3.2.1]octan-3-yl)carbamate. To a stirred solution of 4-chlorobenzaldehyde 1 (500 mg, 3.57 mmol) in DCM (10.0 mL) were added tert-butyl ((1R,3s,5S)-8-azabicyclo[3.2.1]octan-3-yl)carbamate (969.3 mg, 4.28 mmol; CAS #132234-68-5)), and acetic acid (0.05 mL, 0.79 mmol) at 0° C. Resulting reaction mixture was stirred at room temperature for 1 hour. After that, sodium triacetoxy-borohydride (1.51 g, 7.14 mmol) was added to the reaction mixture and stirred overnight. After completion, reaction mixture was diluted with water and extracted with dichloromethane. Combined organic layer was washed with brine, dried over sodium sulphate, filtered and evaporated under reduced pressure. Crude product was purified by combi-flash chromatography (30% ethyl acetate-hexane) to afford tert-butyl ((1R,3s,5S)-8-(4-chlorobenzyl)-8-azabicyclo[3.2.1]octan-3-yl)carbamate (800.0 mg) as an off white solid.

Step-2: Synthesis of (1R,3s,5S)-8-(4-chlorobenzyl)-8-azabicyclo[3.2.1]octan-3-amine.2,2,2-trifluoroacetate. To a stirred solution of tert-butyl ((1R,3s,5S)-8-(4-chlorobenzyl)-8-azabicyclo[3.2.1]-octan-3-yl)carbamate (800.0 mg, 2.28 mmol) in DCM (20.0 mL) was added TFA (1.04 mL, 13.71 mmol) at 0° C. Resulting reaction mixture was stirred at room temperature for 2 hours. After completion, reaction mixture was concentrated under reduced pressure and dried to yield (1R,3s,5S)-8-(4-chlorobenzyl)-8-azabicyclo[3.2.1]octan-3-amine (500 mg) as white solid. 1H NMR (400 MHz, DMSO-d6) δ 1.88-1.96 (m, 4H), 2.04-2.06 (m, 2H), 2.32-2.34 (m, 2H), 3.88-3.90 (m, 2H), 4.18 (bs, 2H), 4.54-4.56 (m, 1H), 7.57 (bs, 4H), 8.13 (bs, 2H).

The steps provided above were generally used to prepare similar azabicyclo[3.2.1]octan-3-amine.2,2,2-trifluoroacetate analogues, for example: by replacing 4-chlorobenzaldehyde (Example 3 and 5) with a) 4-fluorobenzaldehyde (Example 4); b) indole-5-carboxaledhyde (Example 6); c) thiophene-2-carboxaldehyde (Example 7); d) 4-(trifluoromethyl)benzaldehyde (Example 11); e) 2-pyridinecarboxaldehyde (Example 12); f) 3-pyridinecarboxaldehyde (Example 13); g) 4-pyridinecarboxaldehyde (Example 14); h) 2-pyrazinecarboxaldehyde (Example 15); i) 1-methyl-2-imidazolecarboxaldehyde (Example 16); j) isothiazole-5-carbaldehyde (Example 25); k) isothiazole-3-carbaldehyde (Example Synthesis of 1-phenyl-1H-indole-6-carboxylic acid

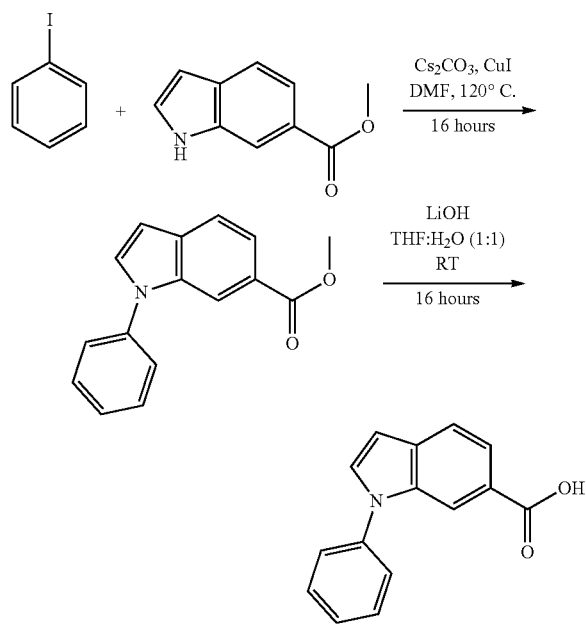

The N-phenyl indole derivative above was synthesized using an Ullman-type reaction between the indole ester and an aryl iodide catalyzed with Copper (I) iodide in the presence of cesium carbonate. The acid intermediate was produced by ester hydrolysis with lithium hydroxide. This process also produced similar intermediates for Examples 18, 21 and 22. In essence, iodobenzene (Example 23) was replaced with: a) 4-iodo-pyridine (Example 18); b) 1-iodo-4-(trifluoromethyl)benzene (Example 21); and c) 1-iodo-4-fluorobenzene (Example 22).

Step-1: Synthesis of methyl 1-phenyl-1H-indole-6-carboxylate. To a stirred degassed solution of iodobenzene (500.0 mg, 2.45 mmol) in DMF (5.0 mL) were added 1H-Indole-6-carboxylic acid methyl ester (698.04 mg, 3.92 mmol), CuI (142.65 mg, 0.50 mmol) and Cs₂CO₃ (1.60 mg, 4.90 mmol). Resulting reaction mixture was heated at 120° C. for 16 hours. After completion, reaction mixture was diluted with water and extracted with ethyl acetate. Combined organic layer was washed with brine, dried over sodium sulphate, filtered and evaporated under reduced pressure. Crude product was purified by combiflash column chromatography (20% ethyl acetate-hexane) to afford methyl 1-phenyl-1H-indole-6-carboxylate (300.0 mg) as brown solid.

Step-2: Synthesis of 1-phenyl-1H-indole-6-carboxylic acid. To a stirred solution of methyl 1-phenyl-1H-indole-6-carboxylate (300.0 mg, 1.20 mmol) in THF and water (6 mL, 1:1) was added LiOH.H₂O (42.94 mg, 1.70 mmol). Resulting reaction mixture was stirred at room temperature for 2 hours. After completion, reaction mixture was concentrated under reduced pressure, diluted with water and pH was adjusted to 4 by using 1 M HCl. Precipitate thus formed was filtered and crude product was triturated with pentane and dried to afford 1-phenyl-1H-indole-6-carboxylic acid (200.0 mg) as an off white solid. LCMS [M−H=235.8].

Intermediate (1R,3s,5S)-8-benzyl-8-azabicyclo[3.2.1]octan-3-EXO-amine, as the free base, can be purchased commercially from companies in the USA (Combi-Blocks; AstaTech; and Synthonix).

Example 1. N-((1R,3s,5S)-8-benzyl-8-azabicyclo[3.2.1]octan-3-yl)-1H-indole-6-carboxamide

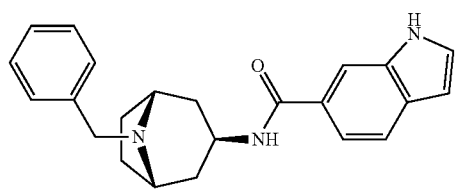 [SMILES: O=C(N[C@@H]1C[C@H]2CC[C@@H](C1)N2Cc1ccccc1)c1ccc2cc[nH]c2c1]

Example 1 was prepared according to the following procedure:

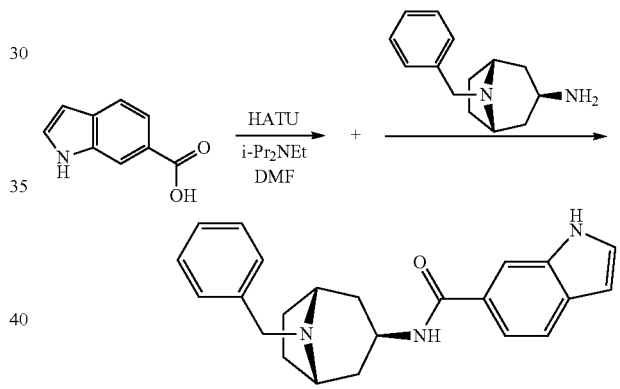

Step 1: 1H-indole-6-carboxylic acid (1.0 g, 6.2 mmol), HATU (1.5 equiv., 6.588 mmol) and N,N-diisopropylethylamine (1.53 mL, 8.784 mmol) were stirred in N,N-dimethylformamide (10 mL) for 10 minutes.

Step 2: To the solution of Step 1 was added 8-benzyl-8-azabicyclo[3.2.1]octan-3-EXO-amine (1000 mg, 4.392 mmol) at room temperature and stirred for 3 hours. The mixture was purified by preparative HPLC to give the title compound as a white solid. $^1$H NMR (400 MHz, DMSO-d6) δ ppm 1.55-1.70 (m, 4H) 1.77 (t, 2H) 1.95-2.10 (m, 2H) 3.17 (bs, 2H) 3.59 (bs, 1H) 4.25 (bs, 1H) 6.46 (bs, 1H) 7.20-7.28 (m, 1H) 7.32 (t, 2H) 7.35-7.41 (m, 2H) 7.48 (bs, 1H) 7.50-7.58 (m, 2H) 7.93 (bs, 1H) 8.09 (d, 1H) 11.32 (br s, 1H). LC-MS (m/z): [M+H]=359.

Example 2. N-((1R,3s,5S)-8-benzyl-8-azabicyclo[3.2.1]octan-3-yl)-1H-pyrrolo[2,3-b]pyridine-6-carboxamide The compound was prepared similarly to Example 1 except that 1H-indole-6-carboxylic acid was replaced with 1H-pyrrolo[2,3-b]pyridine-6-carboxylic acid.

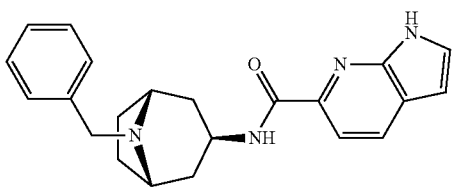 [SMILES: O=C(N[C@@H]1C[C@H]2CC[C@@H](C1)N2Cc1ccccc1)c1ccc2cc[nH]c2n1]

1H NMR (400 MHz, DMSO-d6) δ 1.66-1.78 (m, 6H), 1.99-2.04 (m, 2H), 3.18 (bs, 2H), 3.62 (s, 2H), 4.17-4.23 (m, 1H), 6.54 (s, 1H), 7.23-7.25 (m, 1H), 7.32 (t, J=7.2 Hz, 2H), 7.38-7.40 (m, 2H), 7.66 (bs, 1H), 7.75 (d, J=8.2 Hz, 1H), 8.07-8.11 (m, 2H), 11.75 (s, 1H). LC-MS (m/z): [M+H]=360.

Example 3. N-((1R,3s,5S)-8-(4-chlorobenzyl)-8-azabicyclo[3.2.1]octan-3-yl)-1H-pyrrolo[2,3-b]pyridine-6-carboxamide The compound was prepared similarly to Example 1 except that 1H-indole-6-carboxylic acid was replaced with 1H-pyrrolo[2,3-b]pyridine-6-carboxylic acid and 8-benzyl-8-azabicyclo[3.2.1]octan-3-EXO-amine was replaced with (1R,3s,5S)-8-(4-chlorobenzyl)-8-azabicyclo[3.2.1]octan-3-amine.2,2,2-trifluoroacetate.

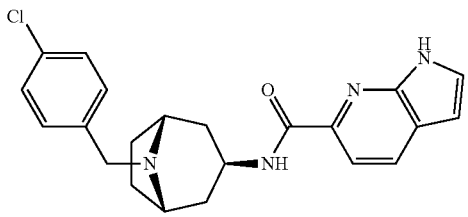

1H NMR (400 MHz, DMSO-d6) δ 1.66-1.78 (m, 6H), 1.97-2.03 (m, 2H), 3.16 (bs, 2H), 3.61 (s, 2H), 4.17-4.22 (m, 1H), 6.54 (s, 1H), 7.37-7.43 (m, 4H), 7.64-7.68 (m, 1H), 7.75 (d, J=8.2 Hz, 1H), 8.07-8.12 (m, 2H), 11.76 (s, 1H). LC-MS (m/z): [M+H]=394.

Example 4. N-((1R,3s,5S)-8-(4-fluorobenzyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(4-fluorobenzyl)-8-azabicyclo[3.2.1]octan-3-amine.2,2,2-trifluoroacetate.

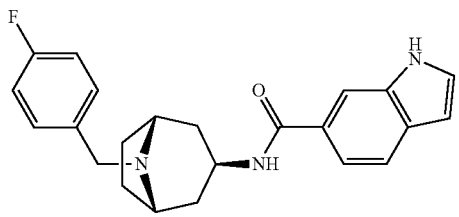 [SMILES: O=C(N[C@@H]1C[C@H]2CC[C@@H](C1)N2Cc1ccc(F)cc1)c1ccc2cc[nH]c2c1]

1H NMR (400 MHz, DMSO-d6) δ 1.63-1.65 (m, 4H), 1.72-1.78 (m, 2H), 1.99-2.01 (m, 2H), 3.16 (bs, 2H), 3.56 (s, 2H), 4.20-4.26 (m, 1H), 6.46 (s, 1H), 7.14 (t, J=8.7 Hz, 2H), 7.38-7.42 (m, 2H), 7.48-7.55 (m, 3H), 7.93 (s, 1H), 8.09 (d, J=7.9 Hz, 1H), 11.32 (s, 1H). LC-MS (m/z): [M+H]=377.

Example 5. N-((1R,3s,5S)-8-(4-chlorobenzyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(4-chlorobenzyl)-8-azabicyclo[3.2.1]octan-3-amine.2,2,2-trifluoroacetate.

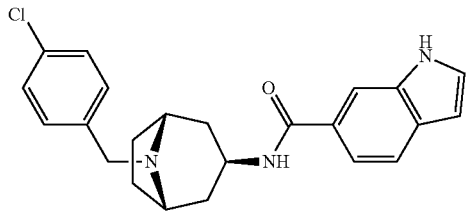 [SMILES: O=C(N[C@@H]1C[C@H]2CC[C@@H](C1)N2Cc1ccc(Cl)cc1)c1ccc2cc[nH]c2c1]

1H NMR (400 MHz, DMSO-d6) δ 1.64-1.66 (m, 4H), 1.73-1.79 (m, 2H), 1.98-2.02 (m, 2H), 3.17 (bs, 2H), 3.59 (s, 2H), 4.18-4.28 (m, 1H), 6.46 (s, 1H), 7.37-7.41 (m, 4H), 7.48-7.55 (m, 3H), 7.93 (s, 1H), 8.08 (d, J=8 Hz, 1H), 11.31 (s, 1H). LC-MS (m/z): [M+H]=393.

Example 6. N-((1R,3s,5S)-8-((1H-indol-5-yl)methyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-((1H-indol-5-yl)methyl)-8-azabicyclo[3.2.1]octan-3-amine.2,2,2-trifluoroacetate.

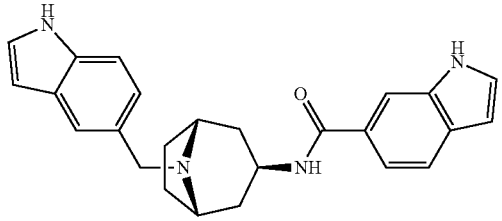 [SMILES: O=C(N[C@@H]1C[C@H]2CC[C@@H](C1)N2Cc1ccc2[nH]ccc2c1)c1ccc2cc[nH]c2c1]

1H NMR (400 MHz, DMSO-d6) δ 1.55-1.66 (m, 4H), 1.74-1.79 (m, 2H), 2.01-2.06 (m, 2H), 3.20 (bs, 2H), 3.62 (s, 2H), 4.19-4.28 (m, 1H), 6.37 (bs, 1H), 6.46 (bs, 1H), 7.12 (d, J=8.6 Hz, 1H), 7.29-7.34 (m, 2H), 7.47-7.53 (m, 4H), 7.93 (s, 1H), 8.08 (d, J=8.2 Hz, 1H), 10.98 (s, 1H), 11.31 (s, 1H). LC-MS (m/z): [M+H]=398.

Example 7. N-((1R,3s,5S)-8-(thiophen-2-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(thiophen-2-ylmethyl)-8-azabicyclo[3.2.1]octan-3-amine.2,2,2-trifluoroacetate.

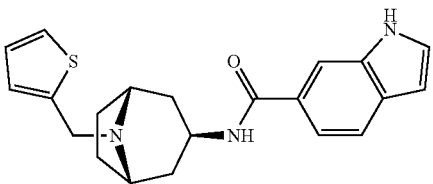 [SMILES: O=C(N[C@@H]1C[C@H]2CC[C@@H](C1)N2Cc1cccs1)c1ccc2cc[nH]c2c1]

1H NMR (400 MHz, DMSO-d6) δ 1.64-1.65 (m, 4H), 1.72-1.78 (m, 2H), 1.97-1.99 (m, 2H), 3.24 (bs, 2H), 3.77 (s, 2H), 4.20-4.24 (m, 1H), 6.46 (s, 1H), 6.95 (s, 2H), 7.39-7.53 (m, 4H), 7.94 (s, 1H), 8.11 (d, J=8.3 Hz, 1H), 11.31 (s, 1H). LC-MS (m/z): [M+H]=365.

Example 8. N-((1R,3s,5S)-8-benzyl-8-azabicyclo[3.2.1]octan-3-yl)-2-methyl-1H-indole-6-carboxamide The compound was prepared similarly to Example 1 except that 1H-indole-6-carboxylic acid was replaced with 2-methyl-1H-indole-6-carboxylic acid.

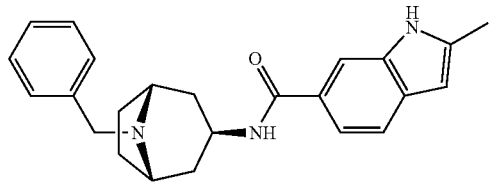 [SMILES: Cc1cc2ccc(C(=O)N[C@@H]3C[C@H]4CC[C@@H](C3)N4Cc3ccccc3)cc2[nH]1]

1H NMR (400 MHz, DMSO-d6) δ 1.63-1.65 (m, 4H), 1.73-1.79 (m, 2H), 1.98-2.02 (m, 2H), 2.40 (s, 3H), 3.17 (bs, 2H), 3.59 (s, 2H), 4.20-4.26 (m, 1H), 6.16 (s, 1H), 7.22-7.25 (m, 1H), 7.31-7.39 (m, 5H), 7.46-7.48 (m, 1H), 7.80 (s, 1H), 8.03 (d, J=8.2 Hz, 1H), 11.13 (s, 1H). LC-MS (m/z): [M+H]=373.

Example 8 was prepared according to the following scheme:

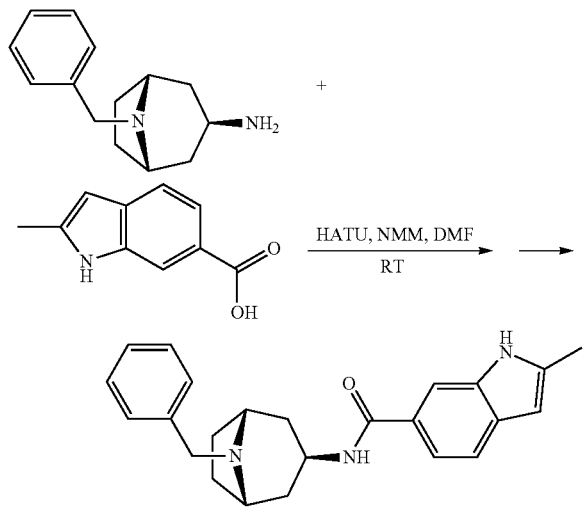

Example 9. N-((1R,3s,5S)-8-benzyl-8-azabicyclo[3.2.1]octan-3-yl)-2,3,4,9-tetrahydro-1H-carbazole-7-carboxamide The compound was prepared similarly to Example 1 except that 1H-indole-6-carboxylic acid was replaced with 2,3,4,9-tetrahydro-1H-carbazole-7-carboxylic acid; was prepared in a similar fashion to Example 1 except that 1H-indole-6-carboxylic acid was replaced with 2,3,4,9-tetrahydro-1H-carbazole-7-carboxylic acid.

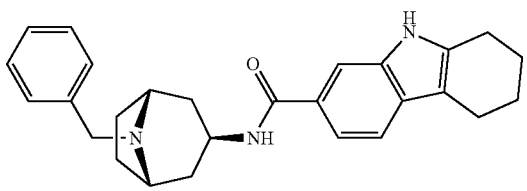 [SMILES: O=C(N[C@@H]1C[C@H]2CC[C@@H](C1)N2Cc1ccccc1)c1ccc2c3c([nH]c2c1)CCCC3]

1H NMR (400 MHz, DMSO-d6) δ 1.58-1.65 (m, 4H), 1.75-1.84 (m, 6H), 2.01 (bs, 2H), 2.58-2.63 (m, 2H), 2.70-2.74 (m, 2H), 3.18 (bs, 2H), 3.60 (bs, 2H), 4.20-4.26 (m, 1H), 7.22-7.26 (m, 1H), 7.31-7.35 (m, 3H), 7.38-7.39 (m, 2H), 7.48 (d, J=8.2 Hz, 1H), 7.79 (s, 1H), 8.03 (d, J=8 Hz, 1H), 10.88 (s, 1H). LC-MS (m/z): [M+H]=413.

Example 10. N-((1R,3s,5S)-8-benzyl-8-azabicyclo[3.2.1]octan-3-yl)-1H-indazole-6-carboxamide The compound was prepared similarly to Example 1 except that 1H-indole-6-carboxylic acid was replaced with 1H-indazole-6-carboxylic acid.

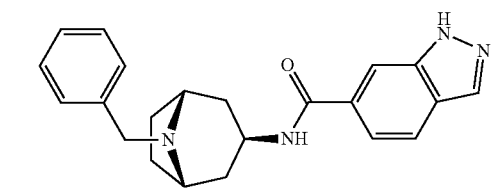 [SMILES: O=C(N[C@@H]1C[C@H]2CC[C@@H](C1)N2Cc1ccccc1)c1ccc2cn[nH]c2c1]

1H NMR (400 MHz, DMSO-d6) δ 1.64-1.66 (m, 4H), 1.74-1.80 (m, 2H), 2.01 (bs, 2H), 3.18 (bs, 2H), 3.58 (s, 2H), 4.21-4.27 (m, 1H), 7.23-7.39 (m, 5H), 7.58 (d, J=8.3 Hz, 1H), 7.79 (d, J=8.3 Hz, 1H), 8.03 (bs, 1H), 8.12 (bs, 1H), 8.32 (d, J=7.6 Hz, 1H), 13.32 (s, 1H). LC-MS (m/z): [M+H]=360.

Example 11. N-((1R,3s,5S)-8-(4-(trifluoromethyl)benzyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(4-(trifluoromethyl)benzyl)-8-azabicyclo[3.2.1]octan-3-amine.2,2,2-trifluoroacetate.

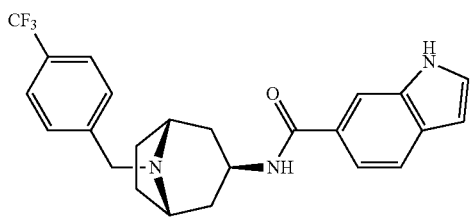 [SMILES: O=C(N[C@@H]1C[C@H]2CC[C@@H](C1)N2Cc1ccc(C(F)(F)F)cc1)c1ccc2cc[nH]c2c1]

1H NMR (400 MHz, DMSO-d6) δ 1.64-1.67 (m, 4H), 1.75-1.81 (m, 2H), 2.00-2.04 (m, 2H), 3.18 (bs, 2H), 3.69 (s, 2H), 4.22-4.26 (m, 1H), 6.46 (s, 1H), 7.48-7.54 (m, 3H), 7.60-7.62 (m, 2H), 7.69-7.71 (m, 2H), 7.93 (s, 1H), 8.10 (d, J=7.8 Hz, 1H), 11.33 (s, 1H). LC-MS (m/z): [M+H]=427.

Example 12. N-((1R,3s,5S)-8-(pyridin-2-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(pyridin-2-ylmethyl)-8-azabicyclo[3.2.1]octan-3-amine.2,2,2-trifluoroacetate.

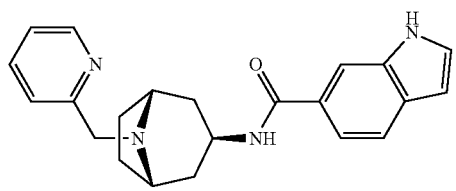 [SMILES: O=C(N[C@@H]1C[C@H]2CC[C@@H](C1)N2Cc1ccccn1)c1ccc2cc[nH]c2c1]

1H NMR (400 MHz, DMSO-d6) δ 1.61-1.68 (m, 4H), 1.78-1.84 (m, 2H), 1.98-2.02 (m, 2H), 3.23 (bs, 2H), 3.73 (s, 2H), 4.22-4.28 (m, 1H), 6.46 (s, 1H), 7.23-7.26 (m, 1H), 7.48-7.56 (m, 4H), 7.76-7.80 (m, 1H), 7.94 (s, 1H), 8.11 (d, J=7.9 Hz, 1H), 8.48 (bs, 1H), 11.32 (s, 1H). LC-MS (m/z): [M+H]=360.

Example 13. N-((1R,3s,5S)-8-(pyridin-3-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(pyridin-3-ylmethyl)-8-azabicyclo[3.2.1]octan-3-amine.2,2,2-trifluoroacetate.

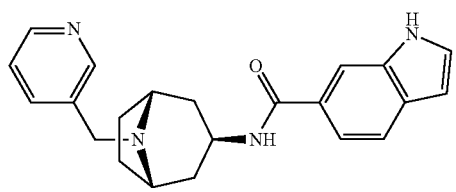 [SMILES: O=C(N[C@@H]1C[C@H]2CC[C@@H](C1)N2Cc1cccnc1)c1ccc2cc[nH]c2c1]

1H NMR (400 MHz, DMSO-d6) δ 1.65-1.66 (m, 4H), 1.73-1.79 (m, 2H), 1.98-2.02 (m, 2H), 3.17 (bs, 2H), 3.62 (s, 2H), 4.18-4.26 (m, 1H), 6.46 (s, 1H), 7.35-7.38 (m, 1H), 7.48-7.56 (m, 3H), 7.76 (d, J=7.4 Hz, 1H), 7.93 (s, 1H), 8.09 (d, J=8 Hz, 1H), 8.46 (d, J=3.7 Hz, 1H), 8.57 (s, 1H), 11.32 (s, 1H). LC-MS (m/z): [M+H]=360.

Example 14. N-((1R,3s,5S)-8-(pyridin-4-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(pyridin-4-ylmethyl)-8-azabicyclo[3.2.1]octan-3-amine.2,2,2-trifluoroacetate.

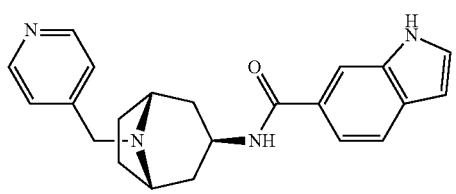 [SMILES: O=C(N[C@@H]1C[C@H]2CC[C@@H](C1)N2Cc1ccncc1)c1ccc2cc[nH]c2c1]

1H NMR (400 MHz, DMSO-d6) δ 1.65-1.67 (m, 4H), 1.73-1.79 (m, 2H), 2.01 (bs, 2H), 3.17 (bs, 2H), 3.63 (s, 2H), 4.20-4.26 (m, 1H), 6.47 (s, 1H), 7.40 (bs, 2H), 7.48-7.54 (m, 3H), 7.93 (s, 1H), 8.10 (d, J=7.4 Hz, 1H), 8.51 (bs, 2H), 11.33 (s, 1H). LC-MS (m/z): [M+H]=360.

Example 15. N-((1R,3s,5S)-8-(pyrazin-2-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(pyrazin-2-ylmethyl)-8-azabicyclo[3.2.1]octan-3-amine.2,2,2-trifluoroacetate.

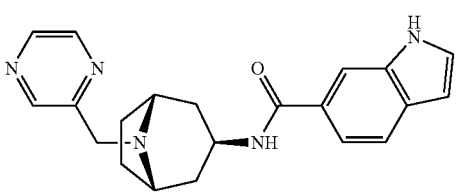 [SMILES: O=C(N[C@@H]1C[C@H]2CC[C@@H](C1)N2Cc1cnccn1)c1ccc2cc[nH]c2c1]

1H NMR (400 MHz, DMSO-d6) δ 1.65-1.69 (m, 4H), 1.78-1.84 (m, 2H), 1.99-2.02 (m, 2H), 3.25 (bs, 2H), 3.79 (s, 2H), 4.22-4.28 (m, 1H), 6.46 (s, 1H), 7.48-7.56 (m, 3H), 7.93 (s, 1H), 8.12 (d, J=8 Hz, 1H), 8.55 (d, J=13.5 Hz, 2H), 8.79 (s, 1H), 11.33 (s, 1H). LC-MS (m/z): [M+H]=361.

Example 16. N-((1R,3s,5S)-8-((1-methyl-1H-imidazol-2-yl)methyl)-8-azabicyclo[3.2.1]octan-3-yl)-1H-indole-6-carboxamide (ZTS-527811)

LC-MS (m/z): [M+H]=363. The compound was prepared similarly to Example 1 except that 8-benzyl-8-azabicyclo[3.2.1]octan-3-EXO-amine was replaced with (1R,3s,5S)-8-((1-methyl-1H-imidazol-2-yl)methyl)-8-azabicyclo[3.2.1]octan-3-amine.2,2,2-trifluoroacetate.

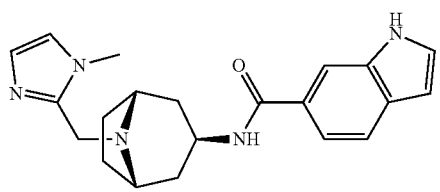 [SMILES: Cn1ccnc1CN1[C@@H]2CC[C@H]1C[C@H](NC(=O)c1ccc3cc[nH]c3c1)C2]

1H NMR (400 MHz, DMSO-d6) δ 1.62-1.64 (m, 4H), 1.69-1.74 (m, 2H), 1.97-1.98 (m, 2H), 3.15 (bs, 2H), 3.62 (s, 2H), 3.73 (s, 3H), 4.20-4.21 (m, 1H), 6.46 (s, 1H), 6.73 (s, 1H), 7.07 (s, 1H), 7.48-7.55 (m, 3H), 7.92 (s, 1H), 8.09 (d, J=8.4 Hz, 1H), 11.32 (s, 1H).

Example 17. N-((1R,3s,5S)-8-phenyl-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-phenyl-8-azabicyclo[3.2.1]octan-3-amine.2,2,2-trifluoroacetate.

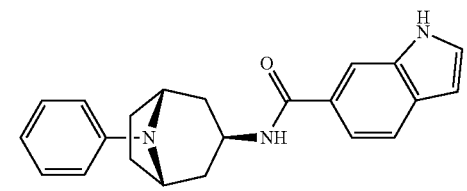 [SMILES: O=C(N[C@@H]1C[C@H]2CC[C@@H](C1)N2c1ccccc1)c1ccc2cc[nH]c2c1]

1H NMR (400 MHz, DMSO-d6) δ 1.58-1.65 (m, 2H), 1.77-1.87 (m, 4H), 1.98-2.03 (m, 2H), 4.31 (bs, 2H), 4.47-4.52 (m, 1H), 6.43 (bs, 1H), 6.60-6.64 (m, 1H), 6.82 (d, J=7.4 Hz, 2H), 7.18-7.21 (m, 2H), 7.45-7.48 (m, 3H), 7.90 (s, 1H), 8.08 (d, J=7.8 Hz, 1H), 11.27 (s, 1H). LC-MS (m/z): [M+H]=345.

Example 17 was prepared according to the following scheme:

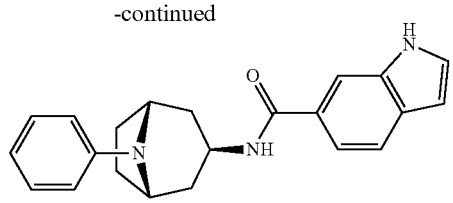

Example 18. N-((1R,3s,5S)-8-benzyl-8-azabicyclo[3.2.1]octan-3-yl)-1-(pyridin-4-yl)-1H-indole-6-carboxamide The compound was prepared similarly to Example 1 except that 1H-indole-6-carboxylic acid was replaced with 1-(pyridin-4-yl)-1H-indole-6-carboxylic acid.

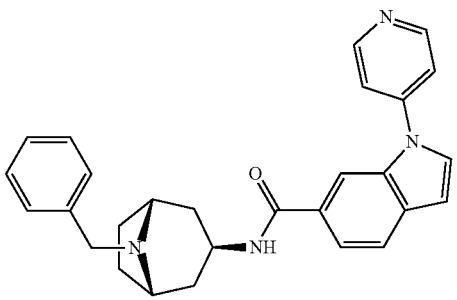

1H NMR (400 MHz, DMSO-d6) δ 1.59-1.65 (m, 4H), 1.72-1.76 (m, 2H), 1.98-2.04 (m, 2H), 3.18 (bs, 2H), 3.55 (s, 2H), 4.21-4.29 (m, 1H), 6.85 (d, J=3.1 Hz, 1H), 7.24-7.36 (m, 5H), 7.71-7.77 (m, 4H), 7.96 (d, J=3.2 Hz, 1H), 8.22-8.26 (m, 2H), 8.76 (d, J=5.8 Hz, 2H). LC-MS (m/z): [M+H]=436.

Example 18 was prepared according to the following scheme:

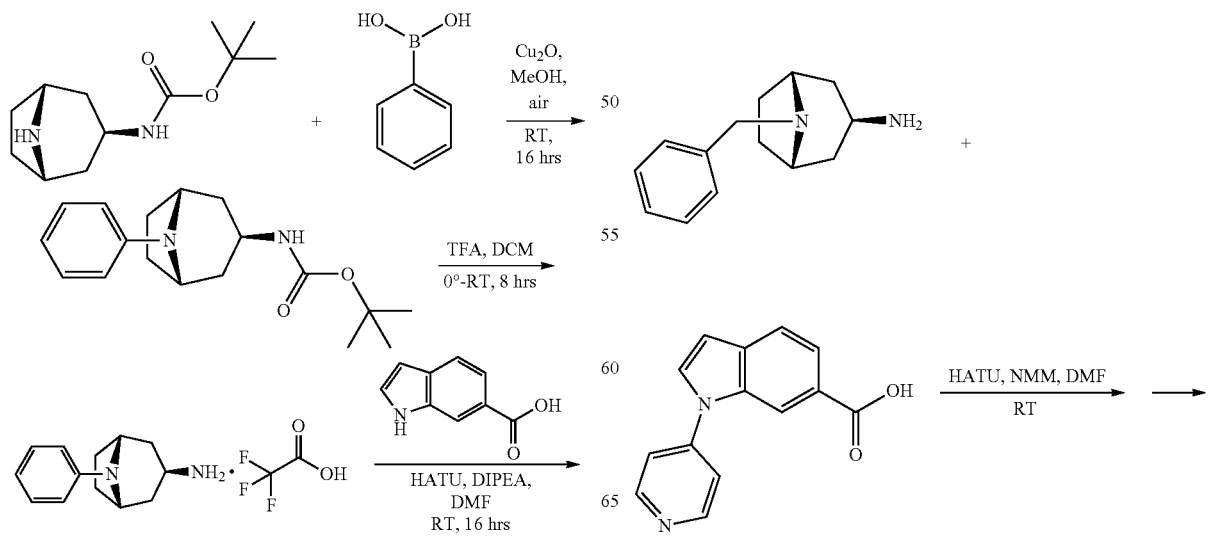

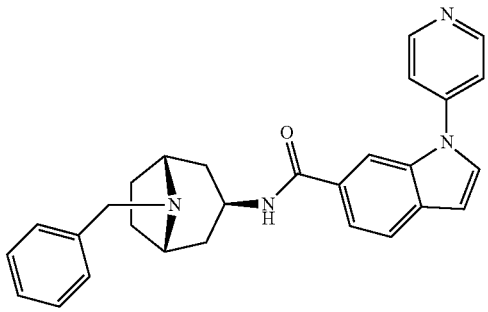

Example 19. N-((1R,3s,5S)-8-benzyl-8-azabicyclo[3.2.1]octan-3-yl)-3-cyano-1H-indole-6-carboxamide The compound was prepared similarly to Example 1 except that 1H-indole-6-carboxylic acid was replaced with 3-cyano-1H-indole-6-carboxylic acid.

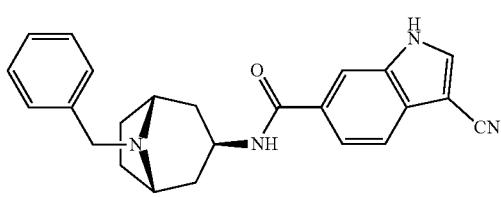

1H NMR (400 MHz, DMSO-d6) δ 1.63-1.65 (m, 4H), 1.76 (t, J=11.3 Hz, 2H), 2.00-2.02 (m, 2H), 3.17 (bs, 2H), 3.58 (s, 2H), 4.21-4.28 (m, 1H), 7.22-7.25 (m, 1H), 7.30-7.38 (m, 4H), 7.67 (d, J=8.4 Hz, 1H), 7.75 (d, J=8.4 Hz, 1H), 8.05 (s, 1H), 8.28 (d, J=8.1 Hz, 1H), 8.38 (s, 1H), 12.43 (s, 1H). LC-MS (m/z): [M+H]=384.

Example 19 was prepared according to the following scheme:

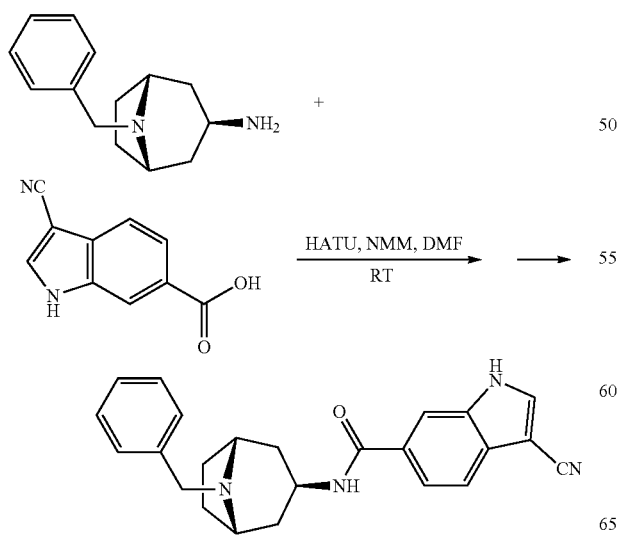

Example 20. N-((1R,3s,5S)-8-benzyl-8-azabicyclo[3.2.1]octan-3-yl)-2-(trifluoromethyl)-1H-indole-6-carboxamide The compound was prepared similarly to Example 1 except that 1H-indole-6-carboxylic acid was replaced with 2-(trifluoromethyl)-1H-indole-6-carboxylic acid.

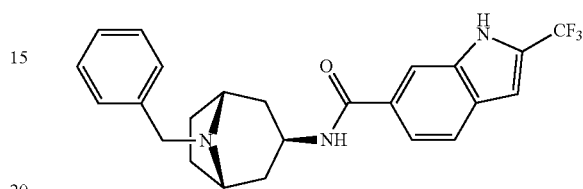

1H NMR (400 MHz, DMSO-d6) δ 1.63-1.65 (m, 4H), 1.75 (t, J=11.6 Hz, 2H), 1.98-2.02 (m, 2H), 3.16 (bs, 2H), 3.60 (s, 2H), 4.19-4.25 (m, 1H), 7.07 (s, 1H), 7.21-7.25 (m, 1H), 7.31-7.38 (m, 4H), 7.63 (d, J=8.5 Hz, 1H), 7.71 (d, J=8.5 Hz, 1H), 7.98 (s, 1H), 8.26 (d, J=8 Hz, 1H), 12.49 (s, 1H). LC-MS (m/z): [M+H]=427.

Example 20 was prepared according to the following scheme:

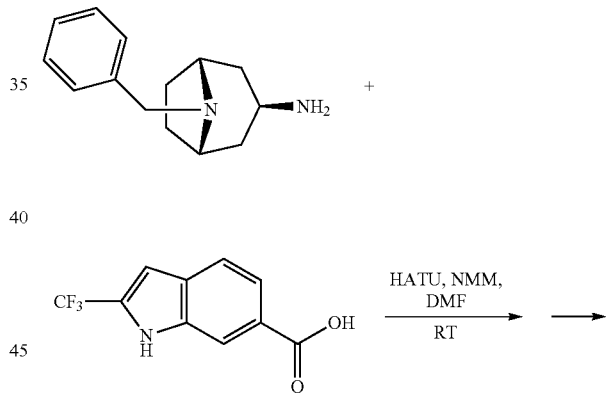

Example 21. N-((1R,3s,5S)-8-benzyl-8-azabicyclo[3.2.1]octan-3-yl)-1-(4-(trifluoromethyl)phenyl)-1H-indole-6-carboxamide The compound was prepared similarly to Example 1 except that 1H-indole-6-carboxylic acid was replaced with 1-(4-(trifluoromethyl)phenyl)-1H-indole-6-carboxylic acid.

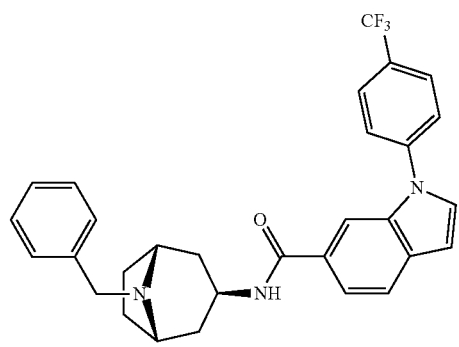

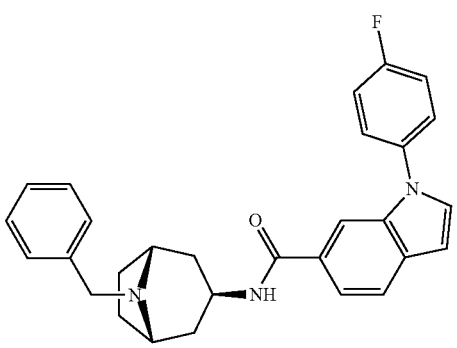

1H NMR (400 MHz, DMSO-d6) δ 1.62-1.64 (m, 4H), 1.70-1.76 (m, 2H), 1.99-2.03 (m, 2H), 3.17 (bs, 2H), 3.55 (s, 2H), 4.20-4.26 (m, 1H), 6.82 (d, J=3.1 Hz, 1H), 7.21-7.24 (m, 1H), 7.30-7.37 (m, 4H), 7.68-7.72 (m, 2H), 7.88-7.90 (m, 3H), 7.98 (d, J=8.4 Hz, 2H), 8.12 (s, 1H), 8.21 (d, J=8.2 Hz, 1H). LC-MS (m/z): [M+H]=503.

Example 21 was prepared according to the following scheme:

1H NMR (400 MHz, DMSO-d6) δ 1.61-1.63 (m, 4H), 1.73 (t, J=11 Hz, 2H), 1.98-2.03 (m, 2H), 3.16 (bs, 2H), 3.55 (s, 2H), 4.20-4.26 (m, 1H), 6.74 (d, J=3 Hz, 1H), 7.21-7.24 (m, 1H), 7.30-7.37 (m, 4H), 7.46 (t, J=8.6 Hz, 2H), 7.64-7.68 (m, 4H), 7.75 (d, J=3.1 Hz, 1H), 7.96 (s, 1H), 8.17 (d, J=8.1 Hz, 1H). LC-MS (m/z): [M+H]=453.

Example 22 was prepared according to the following scheme:

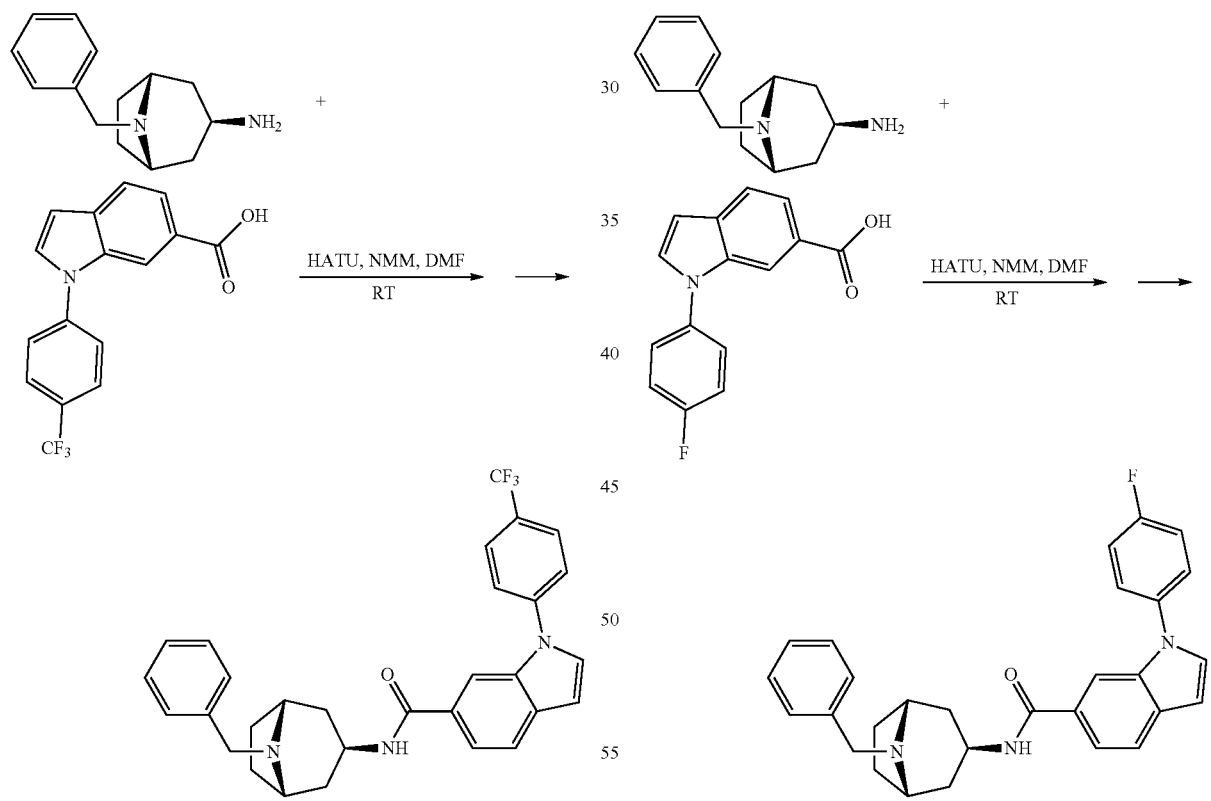

Example 22. N-((1R,3s,5S)-8-benzyl-8-azabicyclo[3.2.1]octan-3-yl)-1-(4-fluorophenyl)-1H-indole-6-carboxamide The compound was prepared similarly to Example 1 except that 1H-indole-6-carboxylic acid was replaced with 1-(4-fluorophenyl)-1H-indole-6-carboxylic acid.

Example 23. N-((1R,3s,5S)-8-benzyl-8-azabicyclo[3.2.1]octan-3-yl)-1-phenyl-1H-indole-6-carboxamide The compound was prepared similarly to Example 1 except that 1H-indole-6-carboxylic acid was replaced with 1-phenyl-1H-indole-6-carboxylic acid.

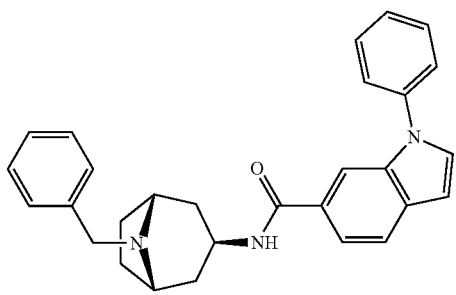

1H NMR (400 MHz, DMSO-d6) δ 1.62-1.64 (m, 4H), 1.71-1.76 (m, 2H), 2.00 (bs, 2H), 3.16 (bs, 2H), 3.56 (s, 2H), 4.19-4.27 (m, 1H), 6.75 (d, J=2.5 Hz, 1H), 7.21-7.25 (m, 1H), 7.30-7.37 (m, 4H), 7.42-7.48 (m, 1H), 7.62-7.69 (m, 6H), 7.79 (d, J=2.8 Hz, 1H), 8.03 (s, 1H), 8.19 (d, J=8 Hz, 1H). LC-MS (m/z): [M+H]=435.

Example 23 was prepared according to the following scheme:

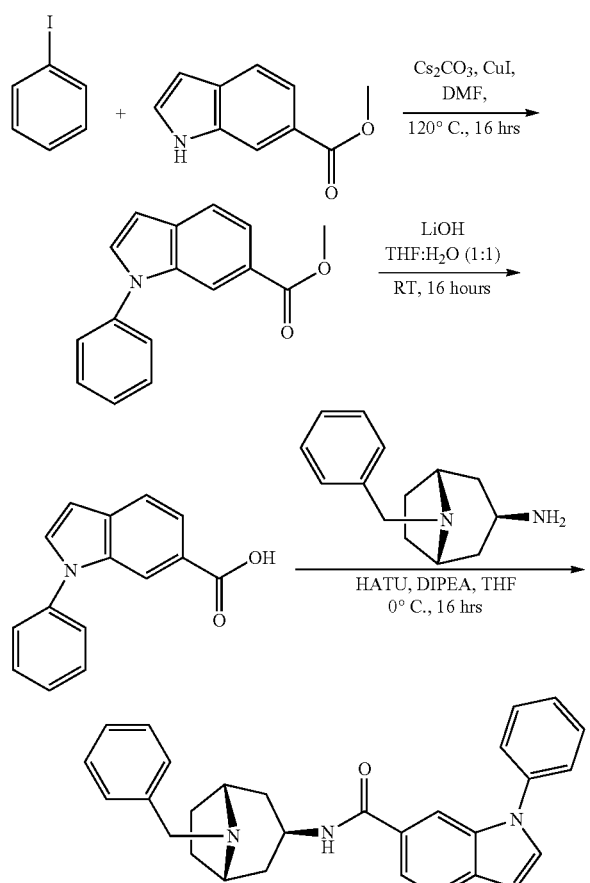

Example 24. N-((1R,3s,5S)-8-benzyl-8-azabicyclo[3.2.1]octan-3-yl)benzofuran-6-carboxamide The compound was prepared similarly to Example 1 except that 1H-indole-6-carboxylic acid was replaced with benzofuran-6-carboxylic acid. LC-MS (m/z): [M+H]=360.

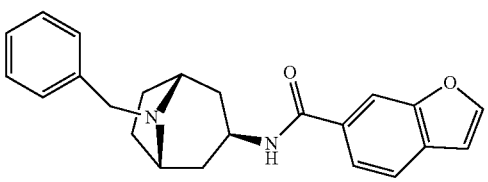

1H NMR (400 MHz, DMSO-d6 at 100° C.) δ 1.77-1.92 (m, 6H), 2.08 (bs, 2H), 3.32 (bs, 2H), 3.75 (bs, 2H), 4.26-4.30 (m, 1H), 6.98 (s, 1H), 7.27-7.29 (m, 1H), 7.33-7.37 (t, J=8.0 Hz, 2H), 7.40-7.44 (m, 2H), 7.68 (d, J=13 Hz, 1H), 7.78 (d, J=8.0 Hz, 1H), 7.90-7.92 (m, 1H), 8.02 (bs, 1H), 8.06 (s, 1H).

Example 25. N-((1R,3s,5S)-8-(isothiazol-5-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(isothiazol-5-ylmethyl)-8-azabicyclo[3.2.1]octan-3-amine.2,2,2-trifluoroacetate. LC-MS (m/z): [M+H]=366.

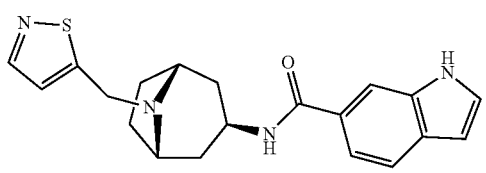

1H NMR (400 MHz, DMSO-d6) δ 1.66-1.68 (m, 4H), 1.74-1.80 (m, 2H), 1.96-1.99 (m, 2H), 3.25 (bs, 2H), 3.93 (s, 2H), 4.21-4.23 (m, 1H), 6.47 (s, 1H), 7.22 (s, 1H), 7.48 (s, 1H), 7.52-7.54 (m, 2H), 7.94 (s, 1H), 8.14 (d, J=7.56 Hz, 1H), 8.46 (s, 1H), 11.33 (s, 1H).

Example 26. N-((1R,3s,5S)-8-(isothiazol-3-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(isothiazol-3-ylmethyl)-8-azabicyclo[3.2.1]octan-3-amine.2,2,2-trifluoroacetate. LC-MS (m/z): [M+H]=366.

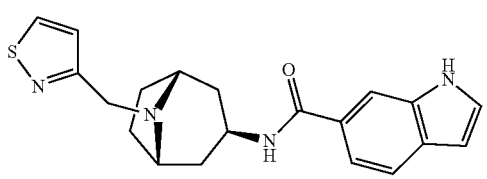

1H NMR (400 MHz, DMSO-d6) δ 1.64-1.66 (m, 4H), 1.75-1.81 (m, 2H), 1.99 (bs, 2H), 3.20 (s, 2H), 3.78 (s, 2H), 4.23-4.27 (m, 1H), 6.46 (s, 1H), 7.38 (d, J=4.36 Hz, 1H), 7.48-7.56 (m, 3H), 7.93 (s, 1H), 8.11 (d, J=8.16 Hz, 1H), 9.01 (bs, 1H), 11.32 (s, 1H).

Example 27. N-((1R,3s,5S)-8-(thiazol-2-ylmethyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(thiazol-2-ylmethyl)-8-azabicyclo[3.2.1]octan-3-amine.2,2,2-trifluoroacetate. LC-MS (m/z): [M+H]=366.

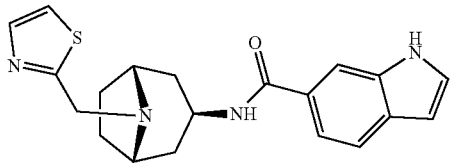

1H NMR (400 MHz, DMSO-d6) δ 1.68-1.69 (m, 4H), 1.78-1.84 (m, 2H), 2.00 (bs, 2H), 3.30 (s, 2H), 3.92 (s, 2H), 4.23-4.26 (m, 1H), 6.47 (s, 1H), 7.48 (s, 1H), 7.52-7.54 (m, 2H), 7.62 (s, 1H), 7.72 (bs, 1H), 7.95 (s, 1H), 8.16 (d, J=7.72 Hz, 1H), 11.33 (s, 1H).

Example 27 was prepared according to the following scheme:

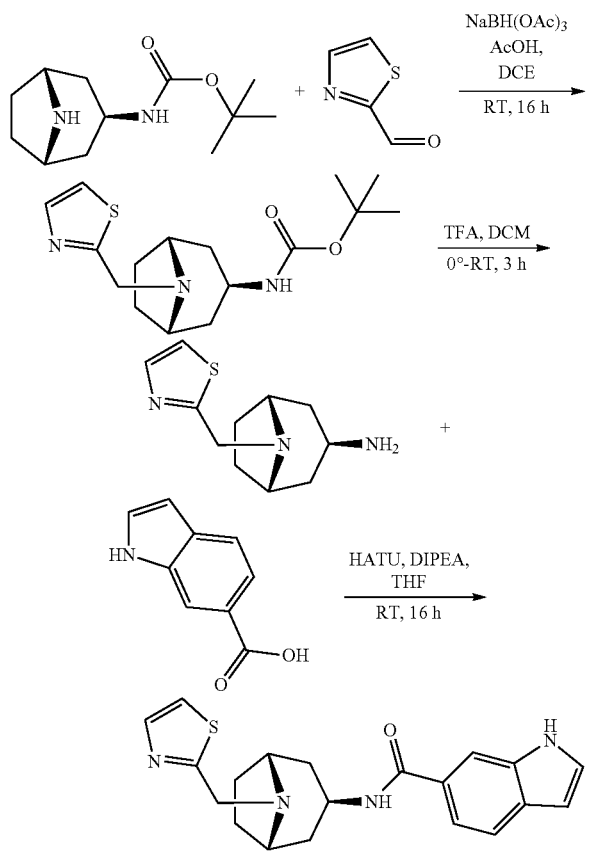

Example 28. N-((1R,3s,5S)-8-((4-methylthiazol-2-yl)methyl)-8-azabicyclo[3.2.1]octan-3-yl)-1H-indole-6-carboxamide The compound was prepared similarly to Example 1 except that 8-benzyl-8-azabicyclo[3.2.1]octan-3-EXO-amine was replaced with (1R,3s,5S)-8-(4-methylthiazol-2-ylmethyl)-8-azabicyclo[3.2.1]octan-3-amine.2,2,2-trifluoroacetate. LC-MS (m/z): [M+H]=380.

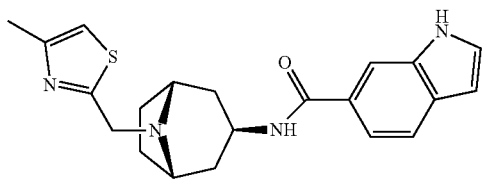

1H NMR (400 MHz, DMSO-d6) δ 1.67-1.69 (m, 4H), 1.76-1.82 (m, 2H), 1.98-2.00 (m, 2H), 2.32 (s, 3H), 3.29 (s, 2H), 3.85 (s, 2H), 4.23-4.26 (m, 1H), 6.47 (s, 1H), 7.13 (s, 1H), 7.47-7.49 (m, 1H), 7.51-7.56 (m, 2H), 7.94 (s, 1H), 8.15 (d, J=8.04 Hz, 1H), 11.32 (s, 1H).

Canine 5-HT2B (c5-HT2B) In-Vitro Assay

CHO-K1 cells stably expressing the canine 5-HT2B receptor were seeded at 20,000 cells per well in 20 µl culture media (DMEM with GlutaMAX™ high glucose+5% dialyzed FBS+10 mM HEPES+1×MEM Non-Essential Amino Acids of a 384-well black plate with clear bottom for at least 18 hours at 37° C. and 5% $CO_2$. The cell plate was loaded with 20 µl/well of the FLIPR© Calcium 5 Assay kit prepared in HBSS containing calcium and magnesium supplemented with 20 mM HEPES and 5 mM Probenecid at pH 7.4 and incubated at 37° C. and 5% $CO_2$ for 30 minutes and then an additional 30 minutes at room temperature. The intracellular calcium response was measured using the FLIPR® Tetra instrument measuring the kinetic response of the calcium 5 dye at an excitation wavelength of 470-495 nm and emission wavelength of 515-575 nm at room temperature. The cells were initially challenged with a 5× concentration of the antagonist (10 µl/well) after an initial baseline recording and the calcium response was recorded for almost 2 minutes. After the completion of the initial antagonist challenge, the cell plate was incubated at room temperature in the FLIPR Tetra® instrument for 10 minutes. Finally, a second kinetic assay was performed after the 10 minute incubation at room temperature to measure the inhibitory response of the $EC_{80}$ concentration of serotonin (15 µl/well) after an initial baseline recording. The $IC_{50}$ concentration was determined for each antagonist tested.

In accordance with the in-vitro assay described above, the $IC_{50}$ affinities for the c5-HT2B receptors for the compounds of the invention are provided in Table 1.

TABLE 1

| Compound Receptor $IC_{50}$ Affinities for c5-HT2B | |
|---|---|
| Example | c5-HT2B (nM) |
| 1 | 0.41 |
| 2 | 0.15 |
| 3 | 1.53 |
| 4 | 0.12 |
| 5 | 0.27 |
| 6 | 0.31 |
| 7 | 1.30 |
| 8 | 4.0 |
| 9 | 112 |
| 10 | 432 |
| 11 | 92.3 |
| 12 | 54.3 |
| 13 | 663 |
| 14 | 2800 |
| 15 | 3700 |

TABLE 1-continued

Compound Receptor IC$_{50}$ Affinities for c5-HT2B

| Example | c5-HT2B (nM) |
|---|---|
| 16 | 8700 |
| 17 | 8280 |
| 18 | 538 |
| 19 | 144 |
| 20 | 21 |
| 21 | 1100 |
| 22 | 32 |
| 23 | 57 |
| 24 | 0.5 |
| 25 | 1.4 |
| 26 | 17.7 |
| 27 | 108 |
| 28 | 200 |

As can be seen in Table 1, the compounds of the invention have an affinity for the c5-HT2B receptor. Based on the data provided in Table 1, the preferred compounds of the invention have a c5-HT2B inhibitory IC$_{50}$ value of <1000 nM. More preferred compounds of the invention have a c5-HT2B inhibitory IC$_{50}$ value<100 nM. Even more preferred compounds of the invention have a c5-HT2B inhibitory IC$_{50}$ value<10 nM.

We claim:
1. A formula (1) compound,

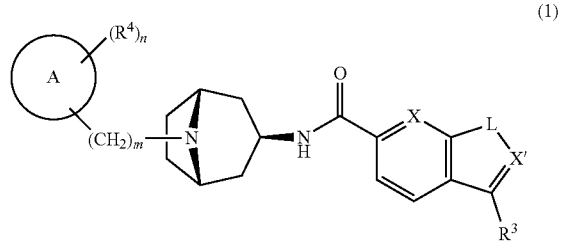

(1)

wherein X is CH or N;
L is NR$^1$ or O;
X' is CR$^2$;
R$^1$ is H, C$_1$-C$_6$alkyl, phenyl or pyridinyl and wherein the phenyl or pyridinyl are each optionally substituted with one or two R$^4$ substituents;
R$^2$ is H, C$_1$-C$_4$alkyl, —CF$_3$ or halo;
R$^3$ is H, cyano, halo, C$_1$-C$_4$alkyl or —CF$_3$;
or R$^2$ and R$^3$ join together to form a 5- or 6-membered carbocyclic ring optionally substituted with methyl, halo or —CF$_3$;
Ring A is phenyl, indolyl, or a 5- or 6-membered heteroaryl ring containing at least one heteroatom selected from the group consisting of N, O and S;
R$^4$ is selected from C$_1$-C$_4$alkyl, halo, cyano or —CF$_3$,
m is the integer 0, 1 or 2;
n is the integer 0, 1, 2 or 3; and when n is the integer 2 or 3 then each R$^4$ can be the same or different; and pharmaceutically acceptable salts thereof.

2. A formula (1) compound of claim 1 wherein Ring A is selected from the group consisting of phenyl, thiophenyl, pyridinyl, thiazolyl and isothiazolyl; L is NR$^1$ and m is the integer 1; and pharmaceutically acceptable salts thereof.

3. A formula (1) compound of claim 1 selected from the group consisting of:

N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-benzyl-8-azabicyclo[3.2.1]octan-3-yl)-2,3,4,9-tetrahydro-1H-carbazole-7-carboxamide;
N-((1R,3s,5S)-8-(4-(trifluoromethyl) benzyl)-8-azabicyclo[3.2.1]octan-3-yl)-1H-indole-6-carboxamide;
N-((1R,3s,5S)-8-(pyridin-2-ylmethyl)-8-azabicyclo[3.2.1]octan-3-yl)-1H-indole-6-carboxamide;
N-((1R,3s,5S)-8-(pyridin-3-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-1-(pyridin-4-yl)-1H-indole-6-carboxamide;
N-((1R,3s,5S)-8-benzyl-8-azabicyclo[3.2.1]octan-3-yl)-3-cyano-1H-indole-6-carboxamide;
N-((1R,3s,5S)-8-benzyl-8-azabicyclo[3.2.1]octan-3-yl)-2-(trifluoromethyl)-1H-indole-6-carboxamide;
N-((1R,3s,5S)-8-benzyl-8-azabicyclo[3.2.1]octan-3-yl)-1-(4-fluorophenyl)-1H-indole-6-carboxamide;
N-((1R,3s,5S)-8-benzyl-8-azabicyclo[3.2.1]octan-3-yl)-1-phenyl-1H-indole-6-carboxamide;
N-((1R,3s,5S)-8-benzyl-8-azabicyclo[3.2.1]octan-3-yl) benzofuran-6-carboxamide;
N-((1R,3s,5S)-8-(isothiazol-5-ylmethyl)-8-azabicyclo[3.2.1]octan-3-yl)-1H-indole-6-carboxamide;
N-((1R,3s,5S)-8-(isothiazol-3-ylmethyl)-8-azabicyclo[3.2.1]octan-3-yl)-1H-indole-6-carboxamide;
N-((1R,3s,5S)-8-(thiazol-2-ylmethyl)-8-azabicyclo[3.2.1]octan-3-yl)-1H-indole-6-carboxamide; and
N-((1R,3s,5S)-8-((4-methylthiazol-2-yl) methyl)-8-azabicyclo[3.2.1]octan-3-yl)-1H-indole-6-carboxamide; and pharmaceutically acceptable salts thereof.

4. A formula (1) compound of claim 3 selected from the group consisting of:

N-((1R,3s,5S)-8-benzyl-8-azabicyclo[3.2.1]octan-3-yl)-1H-indole-6-carboxamide;
N-((1R,3s,5S)-8-benzyl-8-azabicyclo[3.2.1]octan-3-yl)-1H-pyrrolo[2,3-b]pyridine-6-carboxamide;
N-((1R,3s,5S)-8-(4-chlorobenzyl)-8-azabicyclo[3.2.1]octan-3-yl)-1H-pyrrolo[2,3-b]pyridine-6-carboxamide;
N-((1R,3s,5S)-8-(4-fluorobenzyl)-8-azabicyclo[3.2.1]octan-3-yl)-1H-indole-6-carboxamide;
N-((1R,3s,5S)-8-(4-chlorobenzyl)-8-azabicyclo[3.2.1]octan-3-yl)-1H-indole-6-carboxamide;
N-((1R,3s,5S)-8-(thiophen-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-methyl-1H-indole-6-carboxamide;
N-((1R,3s,5S)-8-(4-(trifluoromethyl) benzyl)-8-azabicyclo[3.2.1]octan-3-yl)-1H-indole-6-carboxamide;
N-((1R,3s,5S)-8-(pyridin-2-ylmethyl)-8-azabicyclo[3.2.1]octan-3-yl)-1H-indole-6-carboxamide;
N-((1R,3s,5S)-8-benzyl-8-azabicyclo[3.2.1]octan-3-yl)-2-(trifluoromethyl)-1H-indole-6-carboxamide;
N-((1R,3s,5S)-8-benzyl-8-azabicyclo[3.2.1]octan-3-yl)-1-(4-fluorophenyl)-1H-indole-6-carboxamide;
N-((1R,3s,5S)-8-benzyl-8-azabicyclo[3.2.1]octan-3-yl)-1-phenyl-1H-indole-6-carboxamide;

N-((1R,3s,5S)-8-benzyl-8-azabicyclo[3.2.1]octan-3-yl)
  benzofuran-6-carboxamide;
N-((1R,3s,5S)-8-(isothiazol-5-ylmethyl)-8-azabicyclo
  [3.2.1]octan-3-yl)-1H-indole-6-carboxamide; and
N-((1R,3s,5S)-8-(isothiazol-3-ylmethyl)-8-azabicyclo
  [3.2.1]octan-3-yl)-1H-indole-6-carboxamide; and
  pharmaceutically acceptable salts thereof.

5. A formula (1) compound of claim 4 selected from the group consisting of:
N-((1R,3s,5S)-8-benzyl-8-azabicyclo[3.2.1]octan-3-yl)-
  1H-indole-6-carboxamide;
N-((1R,3s,5S)-8-benzyl-8-azabicyclo[3.2.1]octan-3-yl)-
  1H-pyrrolo[2,3-b]pyridine-6-carboxamide;
N-((1R,3s,5S)-8-(4-chlorobenzyl)-8-azabicyclo[3.2.1]oc-
  tan-3-yl)-1H-pyrrolo[2,3-b]pyridine-6-carboxamide;
N-((1R,3s,5S)-8-(4-fluorobenzyl)-8-azabicyclo[3.2.1]oc-
  tan-3-yl)-1H-indole-6-carboxamide;
N-((1R,3s,5S)-8-(4-chlorobenzyl)-8-azabicyclo[3.2.1]oc-
  tan-3-yl)-1H-indole-6-carboxamide;
N-((1R,3s,5S)-8-(thiophen-2-ylmethyl)-8-azabicyclo
  [3.2.1]octan-3-yl)-1H-indole-6-carboxamide;
N-((1R,3s,5S)-8-benzyl-8-azabicyclo[3.2.1]octan-3-yl)-
  2-methyl-1H-indole-6-carboxamide;
N-((1R,3s,5S)-8-benzyl-8-azabicyclo[3.2.1]octan-3-yl)
  benzofuran-6-carboxamide; and
N-((1R,3s,5S)-8-(isothiazol-5-ylmethyl)-8-azabicyclo
  [3.2.1]octan-3-yl)-1H-indole-6-carboxamide; and
  pharmaceutically acceptable salts thereof.

6. A formula (1) compound of claim 2 that is a Formula (1A) compound

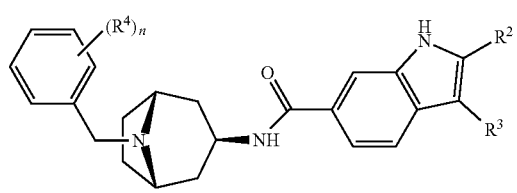

wherein $R^2$ is H, methyl or —$CF_3$; $R^3$ is H, methyl or cyano; and n is the integer 0, 1 or 2;
and pharmaceutically acceptable salts thereof.

7. A formula (1) compound of claim 6 selected from the group consisting of:
N-((1R,3s,5S)-8-benzyl-8-azabicyclo[3.2.1]octan-3-yl)-
  1H-indole-6-carboxamide;
N-((1R,3s,5S)-8-(4-fluorobenzyl)-8-azabicyclo[3.2.1]oc-
  tan-3-yl)-1H-indole-6-carboxamide;
N-((1R,3s,5S)-8-(4-chlorobenzyl)-8-azabicyclo[3.2.1]oc-
  tan-3-yl)-1H-indole-6-carboxamide;
N-((1R,3s,5S)-8-benzyl-8-azabicyclo[3.2.1]octan-3-yl)-
  2-methyl-1H-indole-6-carboxamide;
N-((1R,3s,5S)-8-(4-(trifluoromethyl) benzyl)-8-azabicy-
  clo[3.2.1]octan-3-yl)-1H-indole-6-carboxamide; and
N-((1R,3s,5S)-8-benzyl-8-azabicyclo[3.2.1]octan-3-yl)-
  2-(trifluoromethyl)-1H-indole-6-carboxamide; and
  pharmaceutically acceptable salts thereof.

8. A Formula (1) compound of claim 1 that is a Formula (1B) compound,

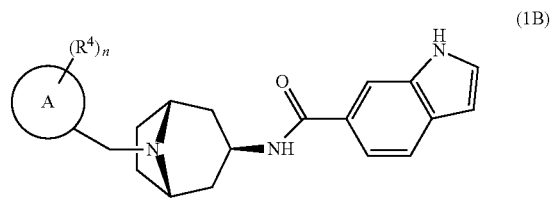

wherein Ring A is selected from the group consisting of indolyl, thiophenyl, pyridinyl, isothiazolyl and thiazolyl; $R^4$ is methyl or halo; and n is the integer 0 or 1;
and pharmaceutically acceptable salts thereof.

9. A Formula (1B) compound of claim 8 selected from the group consisting of:
N-((1R,3s,5S)-8-((1H-indol-5-yl) methyl)-8-azabicyclo
  [3.2.1]octan-3-yl)-1H-indole-6-carboxamide;
N-((1R,3s,5S)-8-(thiophen-2-ylmethyl)-8-azabicyclo
  [3.2.1]octan-3-yl)-1H-indole-6-carboxamide;
N-((1R,3s,5S)-8-(pyridin-2-ylmethyl)-8-azabicyclo
  [3.2.1]octan-3-yl)-1H-indole-6-carboxamide;
N-((1R,3s,5S)-8-(isothiazol-5-ylmethyl)-8-azabicyclo
  [3.2.1]octan-3-yl)-1H-indole-6-carboxamide; and
N-((1R,3s,5S)-8-(isothiazol-3-ylmethyl)-8-azabicyclo
  [3.2.1]octan-3-yl)-1H-indole-6-carboxamide; and
  pharmaceutically acceptable salts thereof.

10. A Formula (1) compound of claim 1 that is a Formula (1C) compound, Formula (1D) compound or Formula (1E) compound,

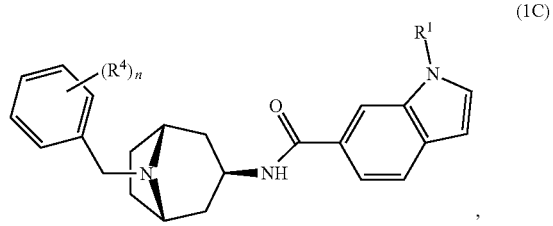

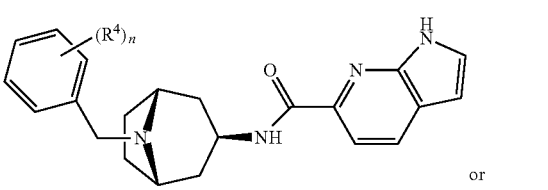

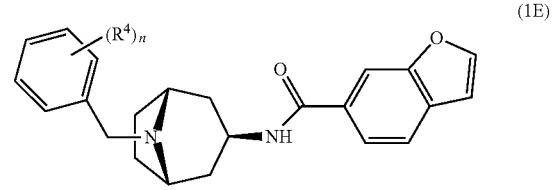

wherein $R^1$ is phenyl optionally substituted with fluoro or chloro; $R^4$ is halo or —$CF_3$ and n is the integer 0 or 1;
and pharmaceutically acceptable salts thereof.

11. A Formula (1C) compound of claim 10 that is N-((1R, 3s,5S)-8-benzyl-8-azabicyclo[3.2.1]octan-3-yl)-1-(4-fluorophenyl)-1H-indole-6-carboxamide or N-((1R,3s,5S)-8-benzyl-8-azabicyclo[3.2.1]octan-3-yl)-1-phenyl-1H-indole-6-carboxamide; a Formula (1D) compound that is N-((1R, 3s,5S)-8-benzyl-8-azabicyclo[3.2.1]octan-3-yl)-1H-pyrrolo

[2,3-b]pyridine-6-carboxamide or N-((1R,3s,5S)-8-(4-chlorobenzyl)-8-azabicyclo[3.2.1]octan-3-yl)-1H-pyrrolo[2,3-b]pyridine-6-carboxamide; or a Formula (1E) compound that is N-((1R,3s,5S)-8-benzyl-8-azabicyclo[3.2.1]octan-3-yl) benzofuran-6-carboxamide; and pharmaceutically acceptable salts thereof.

12. A formula (1) compound of claim 4 selected from the group consisting of:
- N-((1R,3s,5S)-8-benzyl-8-azabicyclo[3.2.1]octan-3-yl)-1H-indole-6-carboxamide;
- N-((1R,3s,5S)-8-benzyl-8-azabicyclo[3.2.1]octan-3-yl)-1H-pyrrolo[2,3-b]pyridine-6-carboxamide;
- N-((1R,3s,5S)-8-(4-chlorobenzyl)-8-azabicyclo[3.2.1]octan-3-yl)-1H-pyrrolo[2,3-b]pyridine-6-carboxamide;
- N-((1R,3s,5S)-8-(4-fluorobenzyl)-8-azabicyclo[3.2.1]octan-3-yl)-1H-indole-6-carboxamide;
- N-((1R,3s,5S)-8-(4-chlorobenzyl)-8-azabicyclo[3.2.1]octan-3-yl)-1H-indole-6-carboxamide;
- N-((1R,3s,5S)-8-(thiophen-2-ylmethyl)-8-azabicyclo[3.2.1]octan-3-yl)-1H-indole-6-carboxamide;
- N-((1R,3s,5S)-8-benzyl-8-azabicyclo[3.2.1]octan-3-yl)-2-methyl-1H-indole-6-carboxamide;
- N-((1R,3s,5S)-8-benzyl-8-azabicyclo[3.2.1]octan-3-yl) benzofuran-6-carboxamide; and
- N-((1R,3s,5S)-8-(isothiazol-5-ylmethyl)-8-azabicyclo[3.2.1]octan-3-yl)-1H-indole-6-carboxamide; and pharmaceutically acceptable salts thereof.

13. A formula (1) compound of claim 12 selected from the group consisting of:
- N-((1R,3s,5S)-8-benzyl-8-azabicyclo[3.2.1]octan-3-yl)-1H-indole-6-carboxamide;
- N-((1R,3s,5S)-8-benzyl-8-azabicyclo[3.2.1]octan-3-yl)-1H-pyrrolo[2,3-b]pyridine-6-carboxamide;
- N-((1R,3s,5S)-8-(4-fluorobenzyl)-8-azabicyclo[3.2.1]octan-3-yl)-1H-indole-6-carboxamide;
- N-((1R,3s,5S)-8-(4-chlorobenzyl)-8-azabicyclo[3.2.1]octan-3-yl)-1H-indole-6-carboxamide; and
- N-((1R,3s,5S)-8-benzyl-8-azabicyclo[3.2.1]octan-3-yl) benzofuran-6-carboxamide; and pharmaceutically acceptable salts thereof.

14. A composition comprising a compound of formula (1) of claim 1 claim 1, or a pharmaceutically acceptable salt thereof.

15. The composition of claim 14, wherein the composition further comprises at least one pharmaceutically acceptable excipient.

16. A method for treating an animal with an effective amount of a compound of formula (1) of claim 1 for myxomatous mitral valve disease (MMVD), congestive heart failure (CHF) and/or asymptomatic heart failure, wherein said animal has myxomatous mitral valve disease (MMVD), congestive heart failure (CHF) and/or asymptomatic heart failure, and wherein said animal is a dog, cat or horse.

17. The method of claim 16, wherein the formula (1) compound is selected from the group consisting of
- N-((1R,3s,5S)-8-benzyl-8-azabicyclo[3.2.1]octan-3-yl)-1H-indole-6-carboxamide;
- N-((1R,3s,5S)-8-benzyl-8-azabicyclo[3.2.1]octan-3-yl)-1H-pyrrolo[2,3-b]pyridine-6-carboxamide;
- N-((1R,3s,5S)-8-(4-chlorobenzyl)-8-azabicyclo[3.2.1]octan-3-yl)-1H-pyrrolo[2,3-b]pyridine-6-carboxamide;
- N-((1R,3s,5S)-8-(4-fluorobenzyl)-8-azabicyclo[3.2.1]octan-3-yl)-1H-indole-6-carboxamide;
- N-((1R,3s,5S)-8-(4-chlorobenzyl)-8-azabicyclo[3.2.1]octan-3-yl)-1H-indole-6-carboxamide;
- N-((1R,3s,5S)-8-(thiophen-2-ylmethyl)-8-azabicyclo[3.2.1]octan-3-yl)-1H-indole-6-carboxamide;
- N-((1R,3s,5S)-8-benzyl-8-azabicyclo[3.2.1]octan-3-yl)-2-methyl-1H-indole-6-carboxamide;
- N-((1R,3s,5S)-8-benzyl-8-azabicyclo[3.2.1]octan-3-yl)-2,3,4,9-tetrahydro-1H-carbazole-7-carboxamide;
- N-((1R,3s,5S)-8-(4-(trifluoromethyl) benzyl)-8-azabicyclo[3.2.1]octan-3-yl)-1H-indole-6-carboxamide;
- N-((1R,3s,5S)-8-(pyridin-2-ylmethyl)-8-azabicyclo[3.2.1]octan-3-yl)-1H-indole-6-carboxamide;
- N-((1R,3s,5S)-8-(pyridin-3-ylmethyl)-8-azabicyclo[3.2.1]octan-3-yl)-1H-indole-6-carboxamide;
- N-((1R,3s,5S)-8-benzyl-8-azabicyclo[3.2.1]octan-3-yl)-1-(pyridin-4-yl)-1H-indole-6-carboxamide;
- N-((1R,3s,5S)-8-benzyl-8-azabicyclo[3.2.1]octan-3-yl)-3-cyano-1H-indole-6-carboxamide;
- N-((1R,3s,5S)-8-benzyl-8-azabicyclo[3.2.1]octan-3-yl)-2-(trifluoromethyl)-1H-indole-6-carboxamide;
- N-((1R,3s,5S)-8-benzyl-8-azabicyclo[3.2.1]octan-3-yl)-1-(4-fluorophenyl)-1H-indole-6-carboxamide;
- N-((1R,3s,5S)-8-benzyl-8-azabicyclo[3.2.1]octan-3-yl)-1-phenyl-1H-indole-6-carboxamide;
- N-((1R,3s,5S)-8-benzyl-8-azabicyclo[3.2.1]octan-3-yl) benzofuran-6-carboxamide;
- N-((1R,3s,5S)-8-(isothiazol-5-ylmethyl)-8-azabicyclo[3.2.1]octan-3-yl)-1H-indole-6-carboxamide;
- N-((1R,3s,5S)-8-(isothiazol-3-ylmethyl)-8-azabicyclo[3.2.1]octan-3-yl)-1H-indole-6-carboxamide;
- N-((1R,3s,5S)-8-(thiazol-2-ylmethyl)-8-azabicyclo[3.2.1]octan-3-yl)-1H-indole-6-carboxamide; and
- N-((1R,3s,5S)-8-((4-methylthiazol-2-yl) methyl)-8-azabicyclo[3.2.1]octan-3-yl)-1H-indole-6-carboxamide; and pharmaceutically acceptable salts thereof.

18. The method of claim 16, wherein the formula (1) compound is selected from the group consisting of
- N-((1R,3s,5S)-8-benzyl-8-azabicyclo[3.2.1]octan-3-yl)-1H-indole-6-carboxamide;
- N-((1R,3s,5S)-8-(4-fluorobenzyl)-8-azabicyclo[3.2.1]octan-3-yl)-1H-indole-6-carboxamide;
- N-((1R,3s,5S)-8-(4-chlorobenzyl)-8-azabicyclo[3.2.1]octan-3-yl)-1H-indole-6-carboxamide;
- N-((1R,3s,5S)-8-benzyl-8-azabicyclo[3.2.1]octan-3-yl)-2-methyl-1H-indole-6-carboxamide;
- N-((1R,3s,5S)-8-(4-(trifluoromethyl) benzyl)-8-azabicyclo[3.2.1]octan-3-yl)-1H-indole-6-carboxamide; and
- N-((1R,3s,5S)-8-benzyl-8-azabicyclo[3.2.1]octan-3-yl)-2-(trifluoromethyl)-1H-indole-6-carboxamide; and pharmaceutically acceptable salts thereof.

19. The method of claim 16, wherein the formula (1) compound is selected from the group consisting of
- N-((1R,3s,5S)-8-benzyl-8-azabicyclo[3.2.1]octan-3-yl)-1-(4-fluorophenyl)-1H-indole-6-carboxamide;
- N-((1R,3s,5S)-8-benzyl-8-azabicyclo[3.2.1]octan-3-yl)-1-phenyl-1H-indole-6-carboxamide;
- N-((1R,3s,5S)-8-benzyl-8-azabicyclo[3.2.1]octan-3-yl)-1H-pyrrolo[2,3-b]pyridine-6-carboxamide;
- N-((1R,3s,5S)-8-(4-chlorobenzyl)-8-azabicyclo[3.2.1]octan-3-yl)-1H-pyrrolo[2,3-b]pyridine-6-carboxamide; and
- N-((1R,3s,5S)-8-benzyl-8-azabicyclo[3.2.1]octan-3-yl) benzofuran-6-carboxamide; and pharmaceutically acceptable salts thereof.

20. The method of claim 16 wherein the companion animal is dog.

21. The compound N-((1R,3s,5S)-8-((1H-indol-5-yl)methyl)-8-azabicyclo[3.2.1]octan-3-yl)-1H-indole-6-carboxamide, or a pharmaceutically acceptable salt thereof.

* * * * *